(12) United States Patent
Tran et al.

(10) Patent No.: US 11,759,221 B2
(45) Date of Patent: Sep. 19, 2023

(54) INTEGRATED THROMBECTOMY AND FILTER DEVICE AND METHODS OF USE

(71) Applicant: eLum Technologies, Inc., Fremont, CA (US)

(72) Inventors: Quang Tran, Atherton, CA (US);
Noelle Bagnall, Irvine, CA (US);
Victor Barajas, Pleasanton, CA (US)

(73) Assignee: eLum Technologies, Inc., Fremont, CA (US)

( * ) Notice: Subject to any disclaimer, the term of this patent is extended or adjusted under 35 U.S.C. 154(b) by 0 days.

(21) Appl. No.: 17/751,481

(22) Filed: May 23, 2022

(65) Prior Publication Data
US 2022/0280175 A1 Sep. 8, 2022

Related U.S. Application Data

(63) Continuation of application No. 16/425,650, filed on May 29, 2019, now Pat. No. 11,399,853.
(Continued)

(51) Int. Cl.
*A61B 17/221* (2006.01)
*A61F 2/01* (2006.01)
(Continued)

(52) U.S. Cl.
CPC ............ *A61B 17/221* (2013.01); *A61L 29/02* (2013.01); *A61B 2017/22094* (2013.01);
(Continued)

(58) Field of Classification Search
CPC ....... A61B 17/221; A61B 2017/22094; A61M 2025/09083; A61F 2002/016; A61F 2/01;
(Continued)

(56) References Cited

U.S. PATENT DOCUMENTS

| 5,827,304 A | 10/1998 | Hart |
| 5,906,627 A | 5/1999 | Spaulding |

(Continued)

FOREIGN PATENT DOCUMENTS

| AT | 404123 T | 8/2008 |
| EP | 1030603 A1 | 8/2000 |

(Continued)

*Primary Examiner* — Wade Miles
*Assistant Examiner* — Bridget E. Rabaglia
(74) *Attorney, Agent, or Firm* — Kilpatrick Townsend & Stockton LLP

(57) ABSTRACT

The invention relates generally to methods and systems for capturing, filtering, or retrieving obstructions or other particulates from a patient's vasculature. In one aspect, device for retrieving an obstruction from a patient is provided that includes an outer delivery shaft and an expandable basket movable between a collapsed configuration and an expanded configuration. The basket is configured to be in the collapsed configuration during delivery and in the expanded configuration during engagement and retrieval of the obstruction. A proximal end of the basket is configured to be centrally and pivotally coupled to the outer delivery shaft. The proximal end and/or a distal end of the basket is movable relative to each other such that a proximal portion of the expandable basket is invertible toward a distal portion of the basket to form a proximally oriented cavity in the expanded configuration to engage and retrieve the obstruction.

27 Claims, 23 Drawing Sheets

Related U.S. Application Data

(60) Provisional application No. 62/836,255, filed on Apr. 19, 2019, provisional application No. 62/701,254, filed on Jul. 20, 2018, provisional application No. 62/697,644, filed on Jul. 13, 2018, provisional application No. 62/677,870, filed on May 30, 2018.

(51) Int. Cl.
  *A61M 25/09* (2006.01)
  *A61B 17/22* (2006.01)
  *A61L 29/02* (2006.01)

(52) U.S. Cl.
  CPC ......... *A61F 2/011* (2020.05); *A61F 2002/016* (2013.01); *A61M 2025/09083* (2013.01)

(58) Field of Classification Search
  CPC .... A61F 2002/018; A61F 2/014; A61F 2/013; A61F 2/0105; A61F 2/0103; A61F 2/012
  See application file for complete search history.

(56) References Cited

U.S. PATENT DOCUMENTS

| | | |
|---|---|---|
| 5,944,730 A | 8/1999 | Nobles et al. |
| 6,066,158 A | 5/2000 | Engelson et al. |
| 6,168,579 B1 | 1/2001 | Tsugita et al. |
| 6,217,526 B1 * | 4/2001 | Frassica ............ A61M 25/0905 600/585 |
| 6,221,006 B1 | 4/2001 | Dubrul et al. |
| 6,238,412 B1 | 5/2001 | Dubrul et al. |
| 6,254,571 B1 | 7/2001 | Hart |
| 6,258,115 B1 | 7/2001 | Dubrul et al. |
| 6,273,876 B1 | 8/2001 | Klima et al. |
| 6,511,897 B2 | 1/2003 | Arima et al. |
| 6,530,939 B1 | 3/2003 | Hopkins et al. |
| 6,589,263 B1 | 7/2003 | Hopkins et al. |
| 6,685,722 B1 | 2/2004 | Rosenbluth et al. |
| 6,699,260 B2 | 3/2004 | Dubrul et al. |
| 6,712,835 B2 | 3/2004 | Mazzocchi et al. |
| 6,755,847 B2 | 6/2004 | Eskuri et al. |
| 6,878,151 B2 | 4/2005 | Carrison et al. |
| 7,056,328 B2 | 6/2006 | Arnott et al. |
| 7,232,432 B2 | 6/2007 | Fulton, III et al. |
| 7,320,698 B2 | 1/2008 | Eskuri et al. |
| 7,331,980 B2 | 2/2008 | Dubrul et al. |
| 7,691,121 B2 | 4/2010 | Rosenbluth et al. |
| 7,780,696 B2 | 8/2010 | Daniel et al. |
| 7,905,896 B2 | 3/2011 | Straub et al. |
| 8,100,935 B2 | 1/2012 | Rosenbluth et al. |
| 8,109,962 B2 | 2/2012 | Pal |
| 8,317,251 B2 | 11/2012 | Nelson |
| 8,317,748 B2 | 11/2012 | Fiorella et al. |
| 8,357,178 B2 | 1/2013 | Pedersen et al. |
| 8,512,352 B2 | 8/2013 | Martin et al. |
| 8,535,334 B2 | 9/2013 | Martin et al. |
| 8,545,526 B2 | 10/2013 | Martin et al. |
| 8,696,622 B2 | 4/2014 | Fiorella et al. |
| 8,715,314 B1 | 5/2014 | Janardhan |
| 8,728,116 B1 | 5/2014 | Janardhan et al. |
| 8,777,976 B2 | 7/2014 | Brady et al. |
| 8,784,441 B2 | 7/2014 | Rosenbluth et al. |
| 8,795,305 B2 | 8/2014 | Martin et al. |
| 8,795,345 B2 | 8/2014 | Pedersen et al. |
| 8,801,748 B2 | 8/2014 | Martin et al. |
| 8,852,205 B2 | 10/2014 | Gilvarry et al. |
| 8,852,226 B2 | 10/2014 | Gilson et al. |
| 8,932,319 B2 | 1/2015 | Martin et al. |
| 8,945,143 B2 | 2/2015 | Cragg et al. |
| 8,979,157 B2 | 3/2015 | Nelson |
| 9,186,487 B2 | 11/2015 | Dubrul et al. |
| 9,204,887 B2 | 12/2015 | Cully et al. |
| 9,254,371 B2 | 2/2016 | Martin et al. |
| 9,271,747 B2 | 3/2016 | Martin |
| 9,271,748 B2 | 3/2016 | Martin |
| 9,308,016 B2 | 4/2016 | Escudero et al. |
| 9,358,094 B2 | 6/2016 | Martin et al. |
| 9,427,252 B2 | 8/2016 | Sos |
| 9,439,664 B2 | 9/2016 | Sos et al. |
| 9,456,834 B2 | 10/2016 | Folk et al. |
| 9,498,604 B2 | 11/2016 | Dubrul et al. |
| 9,597,101 B2 | 3/2017 | Galdonik et al. |
| 9,642,639 B2 | 5/2017 | Brady et al. |
| 9,717,514 B2 | 8/2017 | Martin et al. |
| 9,833,253 B1 | 12/2017 | Ulm |
| 9,848,906 B1 | 12/2017 | Eskridge |
| 9,943,323 B2 | 4/2018 | Martin et al. |
| 10,064,635 B2 | 9/2018 | Martin et al. |
| 10,076,346 B2 | 9/2018 | Martin |
| 10,172,633 B2 | 1/2019 | Martin et al. |
| 11,383,068 B2 | 7/2022 | Tran et al. |
| 11,399,853 B2 * | 8/2022 | Tran .................... A61B 17/221 |
| 2002/0026211 A1 | 2/2002 | Khosravi et al. |
| 2002/0123720 A1 | 9/2002 | Kusleika et al. |
| 2002/0173819 A1 * | 11/2002 | Leeflang ................. A61F 2/014 606/200 |
| 2003/0144686 A1 | 7/2003 | Martinez et al. |
| 2003/0171770 A1 | 9/2003 | Kusleika |
| 2004/0020492 A1 | 2/2004 | Dubrul et al. |
| 2004/0098033 A1 | 5/2004 | Leeflang et al. |
| 2004/0133232 A1 | 7/2004 | Rosenbluth et al. |
| 2004/0199202 A1 | 10/2004 | Dubrul et al. |
| 2004/0260332 A1 | 12/2004 | Dubrul et al. |
| 2004/0260333 A1 | 12/2004 | Dubrul et al. |
| 2005/0090857 A1 | 4/2005 | Kusleika et al. |
| 2005/0131450 A1 | 6/2005 | Nicholson et al. |
| 2005/0177132 A1 | 8/2005 | Lentz et al. |
| 2005/0216050 A1 | 9/2005 | Sepetka et al. |
| 2005/0288656 A1 | 12/2005 | Koerner et al. |
| 2006/0100662 A1 | 5/2006 | Daniel et al. |
| 2006/0161187 A1 | 7/2006 | Levine et al. |
| 2007/0191876 A1 | 8/2007 | Dubrul et al. |
| 2007/0288054 A1 | 12/2007 | Tanaka et al. |
| 2008/0119886 A1 * | 5/2008 | Greenhalgh ...... A61B 17/12172 606/200 |
| 2008/0119889 A1 | 5/2008 | Kusleika |
| 2008/0147170 A1 | 6/2008 | Vrba |
| 2008/0188793 A1 | 8/2008 | Kozak et al. |
| 2009/0069828 A1 | 3/2009 | Martin et al. |
| 2010/0030256 A1 | 2/2010 | Dubrul et al. |
| 2010/0114113 A1 | 5/2010 | Dubrul et al. |
| 2011/0009942 A1 | 1/2011 | Gregorich et al. |
| 2011/0175391 A1 | 7/2011 | Nelson |
| 2011/0213403 A1 | 9/2011 | Aboytes |
| 2013/0345739 A1 | 12/2013 | Brady et al. |
| 2014/0031856 A1 | 1/2014 | Martin et al. |
| 2014/0046358 A1 | 2/2014 | Cully et al. |
| 2014/0058324 A1 | 2/2014 | Salahieh et al. |
| 2014/0236219 A1 | 8/2014 | Dubrul et al. |
| 2014/0260928 A1 | 9/2014 | Janardhan et al. |
| 2014/0309673 A1 | 10/2014 | Dacuycuy et al. |
| 2014/0371781 A1 | 12/2014 | Morgan |
| 2015/0018929 A1 | 1/2015 | Martin et al. |
| 2015/0127035 A1 | 5/2015 | Trapp et al. |
| 2015/0209058 A1 | 7/2015 | Ferrera et al. |
| 2015/0238207 A1 | 8/2015 | Cox et al. |
| 2015/0306311 A1 | 10/2015 | Pinchuk et al. |
| 2016/0022293 A1 | 1/2016 | Dubrul et al. |
| 2016/0096004 A1 | 4/2016 | Gerrans et al. |
| 2016/0220346 A1 | 8/2016 | Bonnette et al. |
| 2016/0331506 A1 | 11/2016 | Korkuch et al. |
| 2016/0367285 A1 | 12/2016 | Sos |
| 2017/0325830 A1 | 11/2017 | Martin et al. |
| 2017/0333675 A1 | 11/2017 | Cottone |
| 2018/0161185 A1 | 6/2018 | Kresslein et al. |
| 2018/0221037 A1 | 8/2018 | Martin et al. |
| 2018/0368865 A1 | 12/2018 | Martin et al. |
| 2019/0015121 A1 | 1/2019 | Martin |

FOREIGN PATENT DOCUMENTS

| | | |
|---|---|---|
| EP | 1617893 A1 | 1/2006 |
| JP | 08308933 A | 11/1996 |
| JP | H10151136 A | 6/1998 |

(56) References Cited

FOREIGN PATENT DOCUMENTS

| | | | |
|---|---|---|---|
| JP | 2002537943 | A | 11/2002 |
| JP | 2006507073 | A | 3/2006 |
| JP | 2006509591 | A | 3/2006 |
| JP | 4731471 | B2 | 4/2011 |
| JP | 2011136180 | A | 7/2011 |
| JP | 2016511106 | A | 4/2016 |
| JP | 2017529222 | A | 10/2017 |
| JP | 2018033491 | A | 3/2018 |
| WO | 9923952 | A1 | 5/1999 |
| WO | 2004093966 | A1 | 11/2004 |
| WO | 2017117092 | A1 | 7/2017 |
| WO | 2018043279 | A1 | 3/2018 |

* cited by examiner

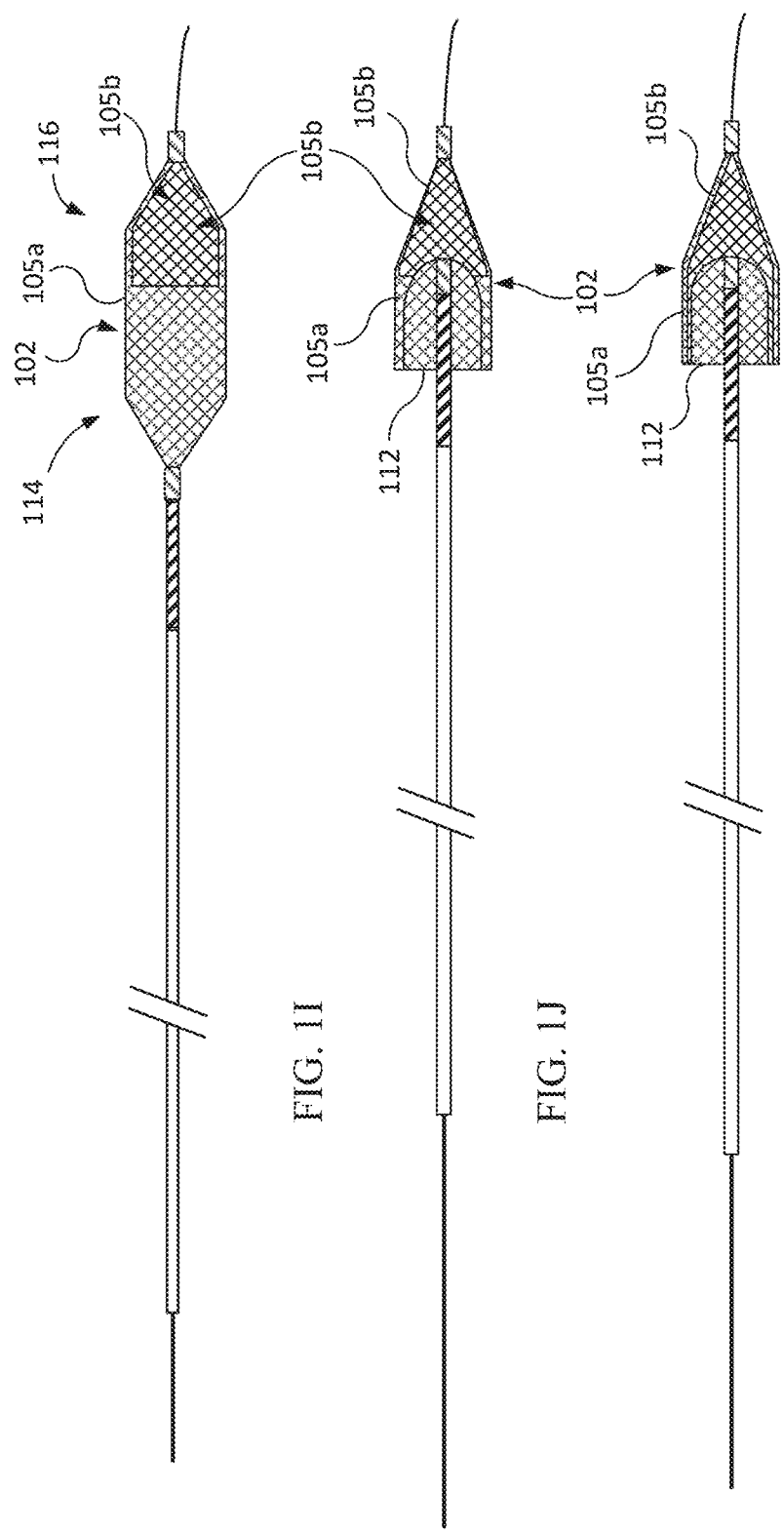

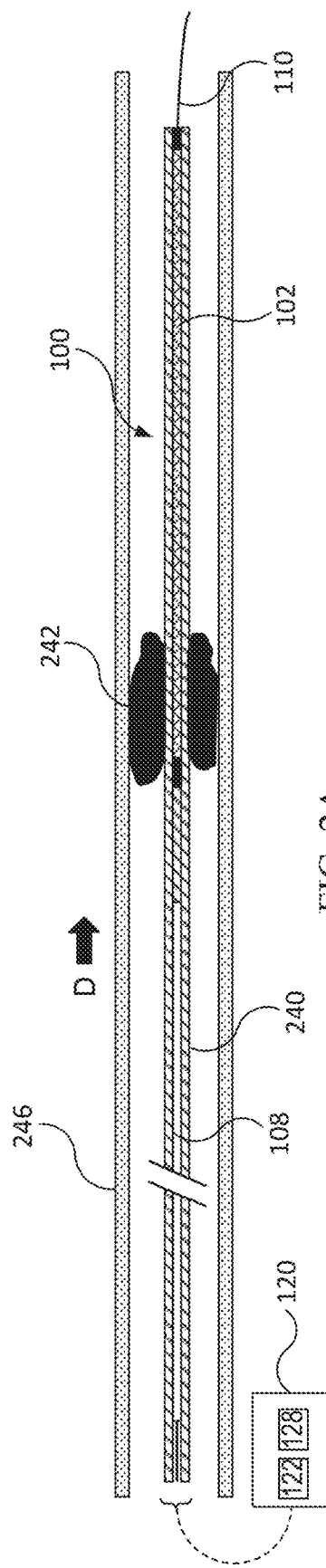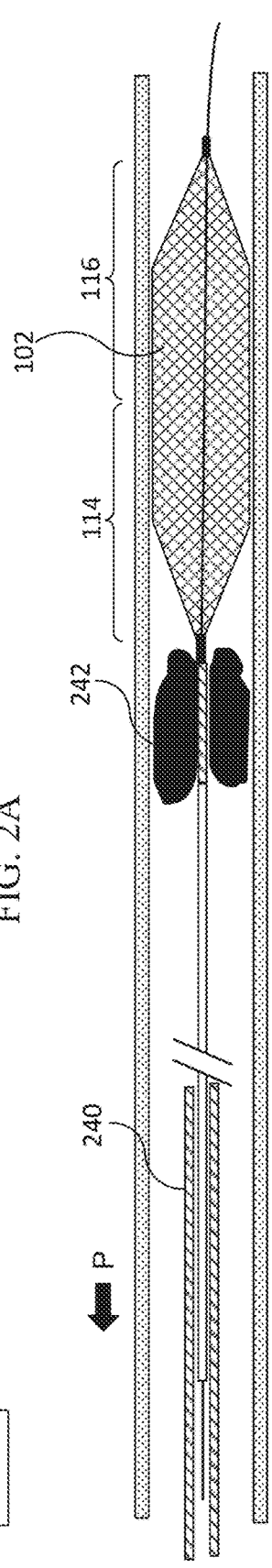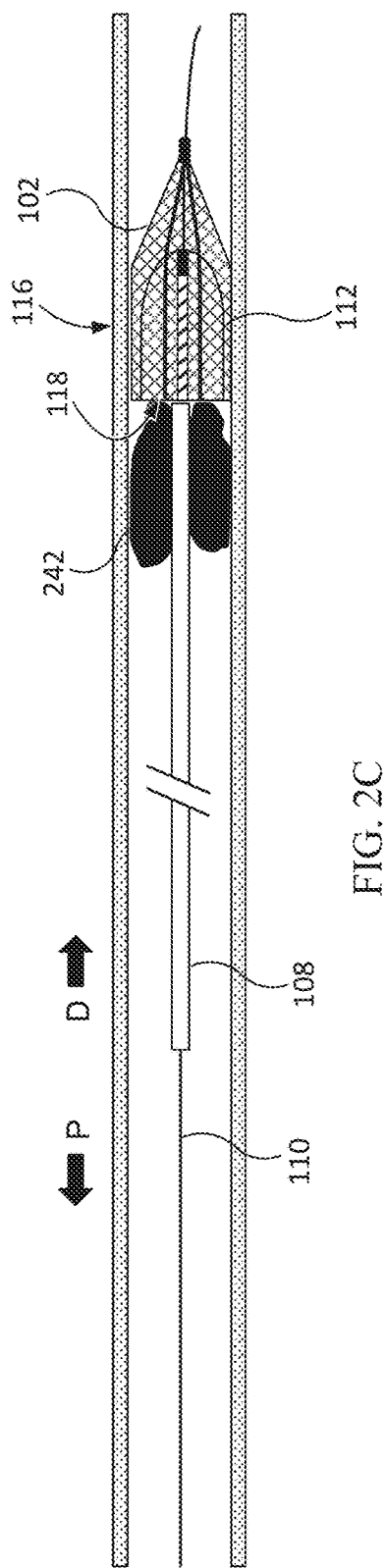

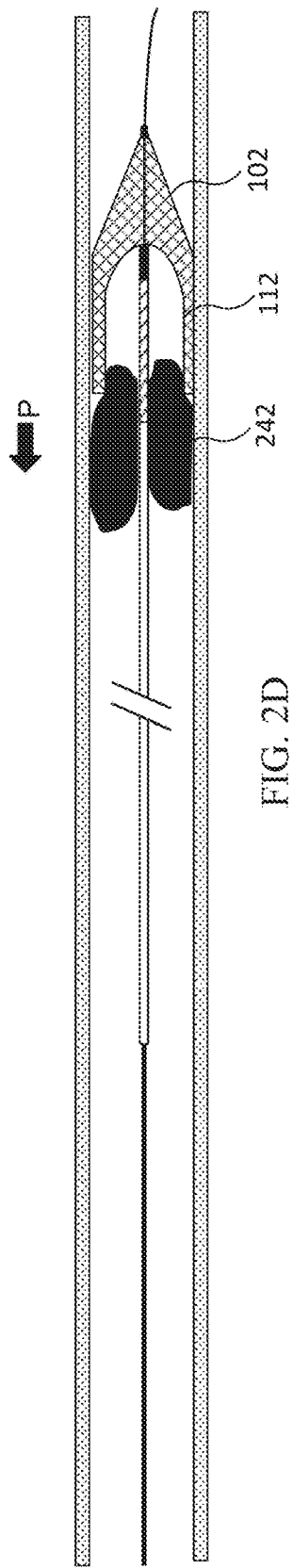
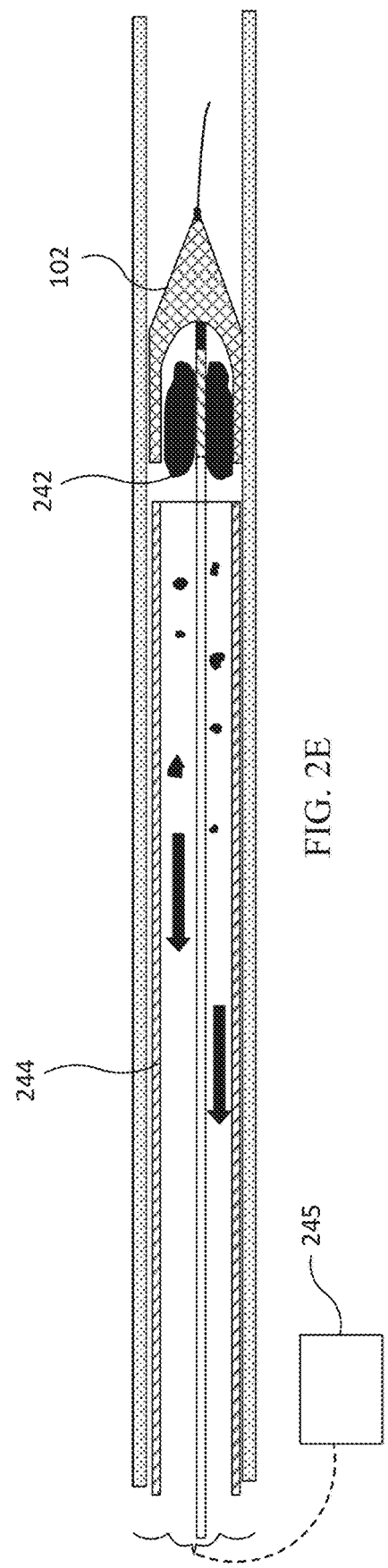
FIG. 2D
FIG. 2E

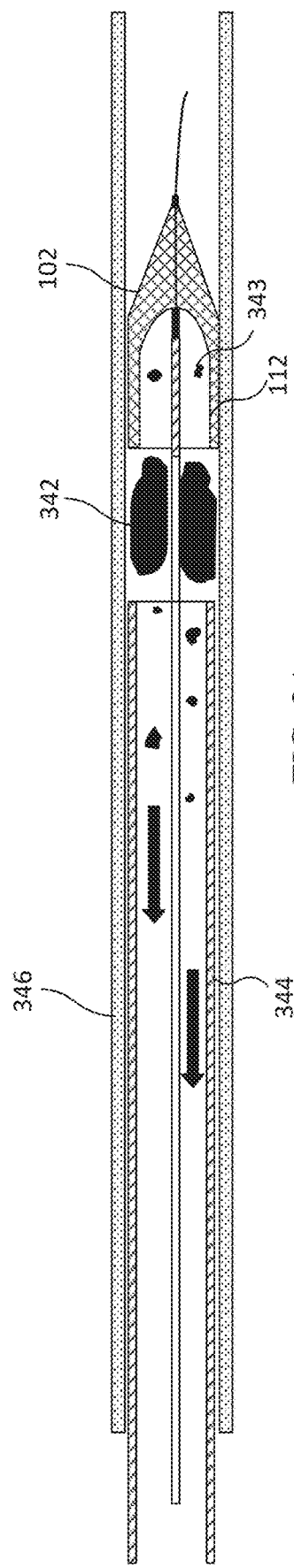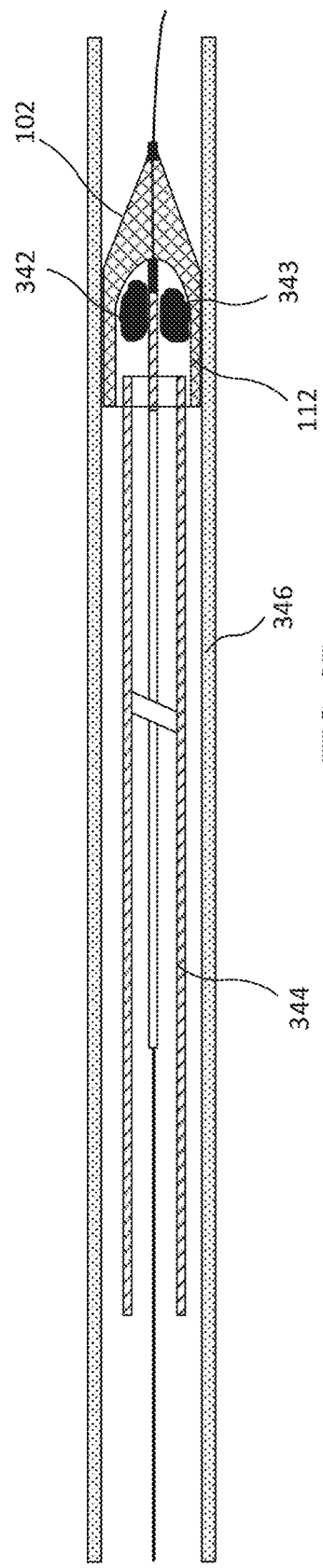

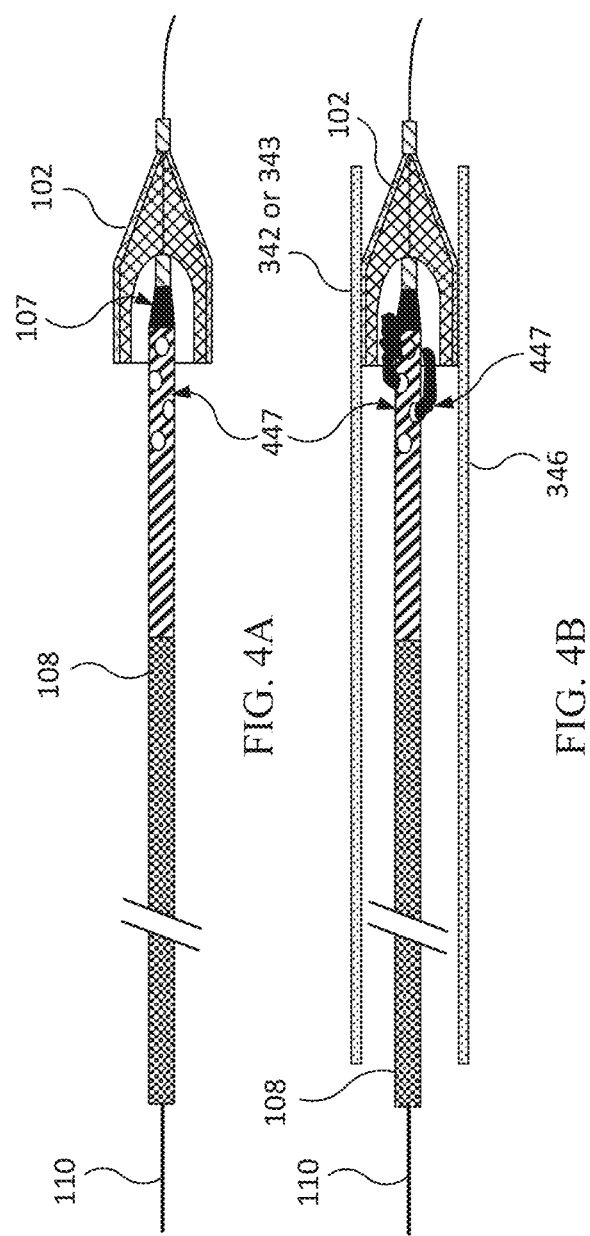

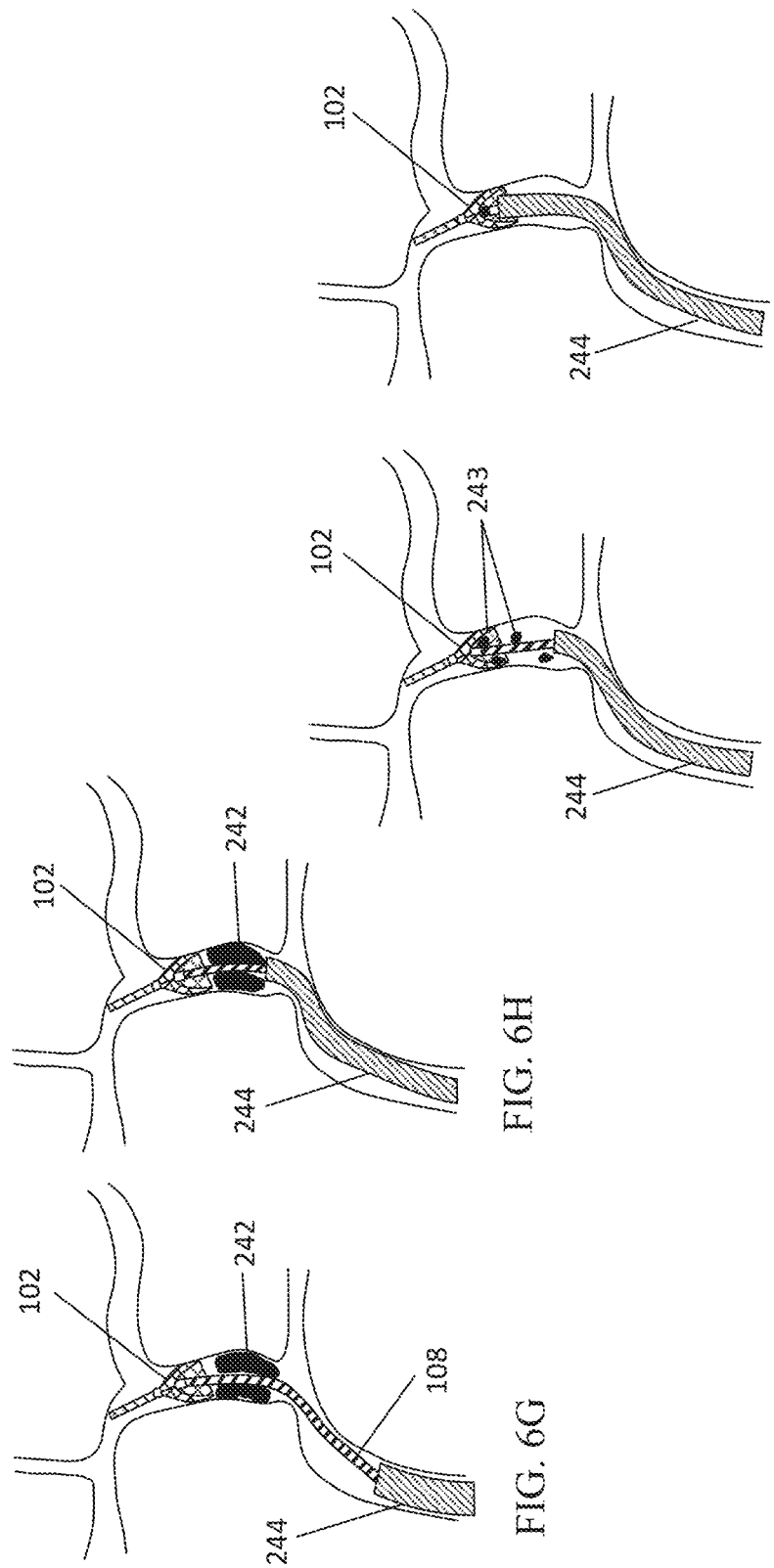

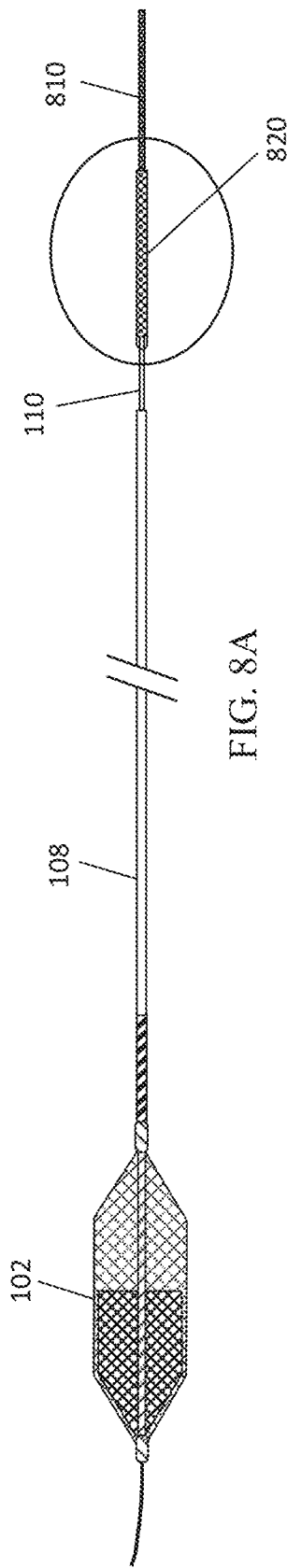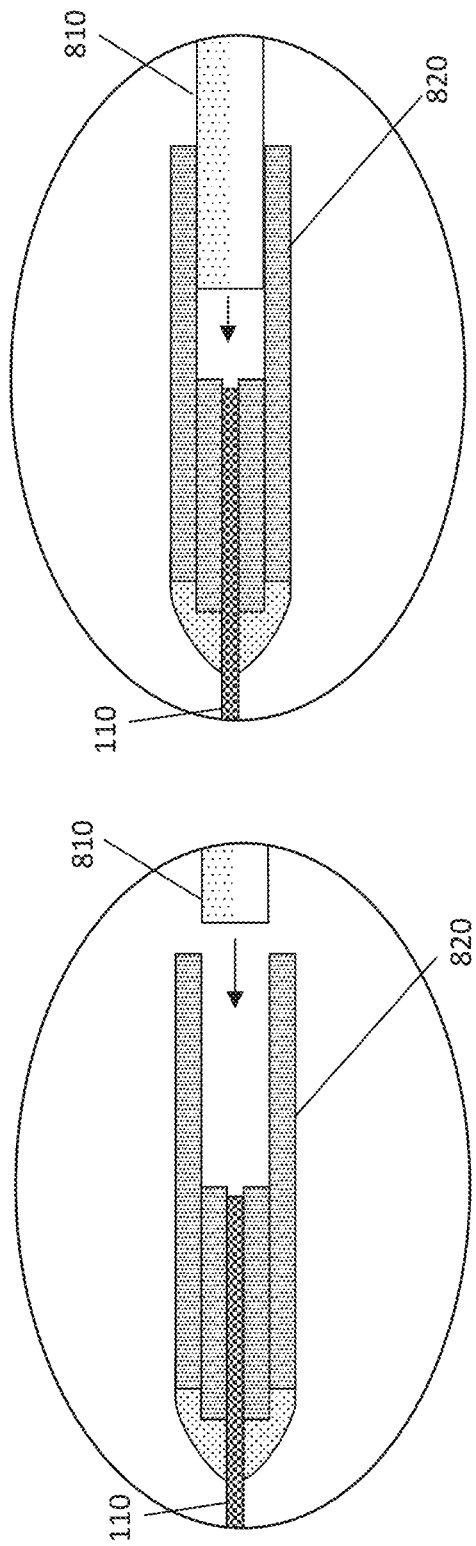
FIG. 8A
FIG. 8B
FIG. 8C

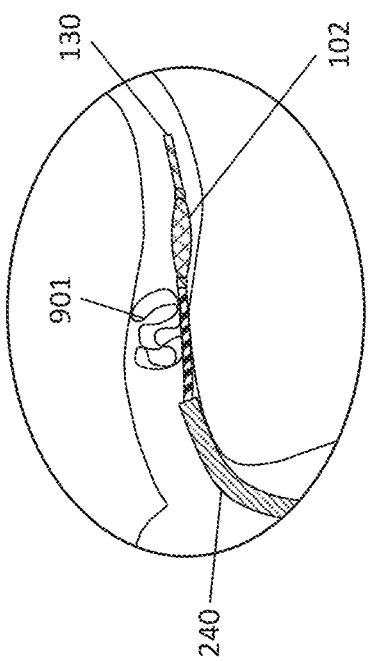
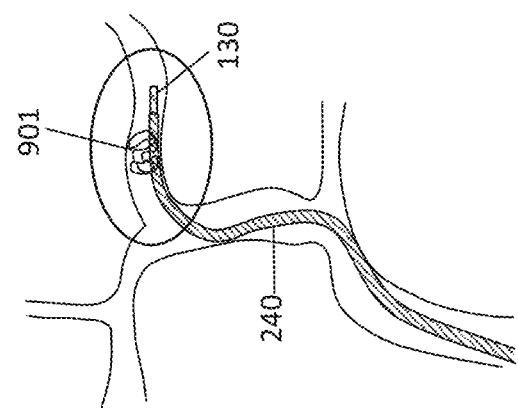
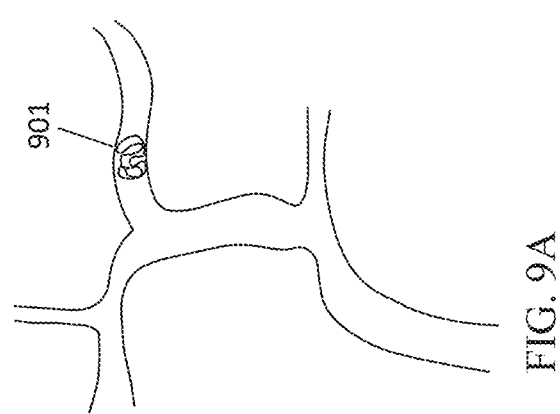

1200

1210 — Advance an intravascular device into a vasculature of the patient. The intravascular device includes an expandable basket movable between a collapsed configuration and an expanded configuration and having a proximal end and a distal end. The proximal end is configured to be centrally and pivotally coupled to an outer delivery shaft.

1220 — Deploy the expandable basket from the collapsed configuration to the expanded configuration by moving at least one of the proximal end or distal end relative to each other to invert a proximal portion of the expandable basket toward a distal portion of the expandable basket to form a proximally oriented cavity in the expanded configuration.

1230 — Anchor the intravascular device distal of an obstruction.

1240 — Capture the at least one released particulate within the proximally oriented cavity of the expandable basket.

*FIG. 12*

INTEGRATED THROMBECTOMY AND FILTER DEVICE AND METHODS OF USE

CROSS-REFERENCE TO RELATED APPLICATIONS

The present application is a Continuation of U.S. patent application Ser. No. 16/425,650 filed May 29, 2019 (Allowed); which claims the benefit of U.S. Provisional Appln Nos. 62/677,870 filed May 30, 2018; 62/697,644 filed Jul. 13, 2018; 62/701,254 filed Jul. 20, 2018; and 62/836,255 filed Apr. 19, 2019; the full disclosures which are incorporated herein by reference in their entirety for all purposes.

BACKGROUND OF THE INVENTION

This application relates generally to methods and systems for retrieving, capturing, filtering, or removing obstructions or other particulates (thrombus, clot, emboli, foreign body (e.g., loose aneurysm coils)) from a patient's vasculature, and more specifically relates to integrated thrombectomy and filtering devices and methods of use.

Typically, acute ischemic stroke is caused by thrombotic or embolic occlusion of a cerebral artery obstructing flow therethrough. Preserving salvageable tissue in a patient's ischemic penumbra by restoring blood flow is a primary objective of acute ischemic stroke therapies. Recanalization therapies may include administration of intravenous tissue-type plasminogen activators or endovascular intra-arterial techniques for clot retrieval (e.g., mechanical thrombectomy).

Currently, a common mechanical thrombectomy technique includes positioning a self-expanding stent on a delivery wire within a blood vessel and aligning the stent with a clot. The stent is configured to engage the clot and be withdrawn with the clot out of a patient. In some situations, a clot may be strongly adhered to a vessel wall. Because self-expandable stents are generally maintained in an open position via internal radial force, such stents tend to compress when encountering radial resistance during retrieval. For example, a pull force applied to the proximal end of such a stent translates into compressive force causing the stent to compress and collapse. A partially compressed stent may slide through a channel created through the clot during the stent delivery or placement process which may leave behind residual clots or fragments still adhered to the vessel wall. Another common mechanical thrombectomy technique includes directly aspirating a clot. Such aspiration techniques may also leave behind residual clots or fragments that may migrate distally, potentially occluding smaller downstream vessels. Therefore, it would be desirable to provide improved systems and methods for retrieving, capturing, filtering, or removing obstructions or other particulates from a patient's vasculature.

BRIEF SUMMARY OF THE INVENTION

The invention relates generally to methods and systems for retrieving, capturing, filtering, or removing obstructions or other particulates from a patient's vasculature, and more specifically relates to integrated thrombectomy and filtering devices and methods of use. The vasculature contemplated herein may include a neurovasculature, a pulmonary vasculature, a peripheral vasculature, or a coronary vasculature. The methods and systems described herein may be used for any suitable medical procedure. For example, they may be used for the neurovascular procedure, a pulmonary vasculature procedure, a coronary vasculature procedure, or a peripheral vasculature procedure. The disclosure contemplates removal of obstructions that may include a thrombus, emboli, or clot. The disclosure also contemplates the removal of obstructions including foreign body objects (e.g., a dislodged implant, a dislodged aneurysm coil). Such methods and systems may be suitable for use during an intravascular procedure to restore blood flow through a blocked or obstructed vessel (e.g., arterial lumen). For example, the methods and systems may be configured to remove clots from a neurovascular vessel or lumen (e.g., in the head, neck, or brain) or provide protection from distal emboli (e.g., filtering) during removal of the clot, an aspiration procedure, or other procedure (e.g., to break up or dissolve the clot). In one aspect, an intravascular device for retrieving an obstruction from a patient is provided that includes an outer delivery shaft and an expandable basket movable between a collapsed configuration and an expanded configuration. The expandable basket is configured to be in the collapsed configuration during delivery into a vasculature of the patient and in the expanded configuration during engagement and retrieval of the obstruction. The expandable basket includes a proximal end and a distal end. The proximal end is configured to be centrally and pivotally coupled to the outer delivery shaft. At least one of the proximal end or the distal end is movable relative to each other such that a proximal portion of the expandable basket is invertible towards a distal portion of the expandable basket to form a proximally oriented cavity in the expanded configuration to engage and retrieve the obstruction.

In some embodiments, a distal portion of the outer delivery shaft is pivotally coupled to the proximal end of the expandable basket. The intravascular device may include an inner core wire extending (e.g., coaxially) through the outer delivery shaft with a distal portion of the inner core wire coupled to the distal end of the expandable basket. In some aspects of the invention, the proximal end of the expandable basket is axially movable relative to the distal end to invert the proximal portion of the expandable basket towards the distal portion of the expandable basket to form the proximally oriented cavity. In certain embodiments, the distal end of the expandable basket is axially movable relative to the proximal end to invert the proximal portion of the expandable basket towards the distal portion of the expandable basket to form the proximally oriented cavity. In some embodiments, the proximally oriented cavity has a cup-shaped cavity.

In some embodiments, the proximal end of the expandable basket is spaced radially inward from a peripheral edge of the distal portion of the expandable basket when the proximal portion is inverted towards the distal portion of the expandable basket. The axial positions of the proximal and distal ends of the expandable basket are securable relative to each other after the proximal portion of the expandable basket is inverted towards the distal portion of the expandable basket to form the proximally oriented cavity. In some embodiments, the proximal and distal ends of the expandable basket are securable relative to each other in a plurality of axial positions such that a shape or size of the proximally oriented cavity is adjustable.

In certain aspects of the inventions, the distal portion of the expandable basket includes a pre-set conical configuration. In certain embodiments, the intravascular device includes an aspiration system configured to aspirate a retrieved obstruction from the proximally oriented cavity of the expandable basket out of the patient. In certain embodiments, the intravascular device includes a delivery catheter configured to position the expandable basket distal to the obstruction in the collapsed configuration, the delivery catheter extending around at least a portion of the expandable basket. In some embodiments, the expandable basket is configured to be moved to the collapsed configuration from the expanded configuration for removal from the patient via the delivery catheter after removal of a retrieved obstruction.

In yet further embodiments, the intravascular device includes a handle coupled to the outer delivery shaft and the inner core wire, the handle including one or more locking mechanisms configured to secure a position of the outer delivery shaft relative to a position of the inner core wire. In some embodiments, the expandable basket is constructed from a radiopaque material. The expandable basket may be fluoroscopically viewable at least in part due to the radiopaque material. In some embodiments, the device includes a coil extending around a distal tip of the inner core wire. In some embodiments, the coil (or at least a portion thereof) may be made of platinum, platinum alloy, or otherwise a material that includes platinum. In certain embodiments, the inner core wire tapers in diameter from a proximal portion to a distal portion of the inner core wire. In some embodiments, the inner core wire includes a cylindrical portion and a flattened portion. The flattened portion may be at a distal end of the inner core wire. In some embodiments, the expandable basket comprises a filter to trap particulates released during aspiration or removal of the obstruction to prevent distal migration of particulates of the obstruction.

In some embodiments, an extender wire may be coupled to the inner core wire. For example, the extender wire may be releasably coupled to the inner core wire. The extender wire may be releasably coupled to the inner core wire via one or more extender hypotubes. In some embodiments, a delivery catheter may be exchanged for a different catheter (e.g., an aspiration catheter) over the extender wire.

In yet other embodiments, the expandable basket includes support ribs. In some embodiments, a portion of the expandable basket includes multiple layers. The multiple layers may include an inner layer and an outer layer. In certain embodiments, the inner layer is configured to expand to a larger diameter relative to the outer layer when the expandable basket is moved to a partially expanded configuration between the collapsed configuration and expanded configuration. In some embodiments, the intravascular device includes an aspiration catheter, the aspiration catheter configured to be at least partially positioned within the proximally oriented cavity during an aspiration procedure In another aspect of the invention, a method for retrieving a thrombus (or some other obstruction) from a neurovasculature of a patient to prevent or treat ischemic stroke is provided that includes the steps of: advancing a neurovascular device distally of a thrombus within a patient, the neurovascular device comprising an expandable basket movable between a collapsed configuration and an expanded configuration and having a proximal end and a distal end, the proximal end configured to be centrally and pivotally coupled to an outer delivery shaft; deploying the expandable basket from the collapsed configuration to the expanded configuration by moving at least one of the proximal end or distal end relative to each other to invert a proximal portion of the expandable basket towards a distal portion of the expandable basket to form a proximally oriented cavity, the proximally oriented cavity having a proximally oriented cavity in the expanded configuration to engage and retrieve the thrombus; retracting the expandable basket proximally to engage and retrieve the thrombus into the proximally oriented cavity.

In some embodiments, the method includes pivoting the outer delivery shaft relative to the expandable basket as the expandable basket is pulled proximally through the neurovasculature. In certain embodiments, the intravascular device includes the outer delivery shaft and an inner core wire extending coaxially through the outer delivery shaft with a distal portion of the inner core wire coupled to the distal end of the expandable basket. In some embodiments, moving the expandable basket from the collapsed configuration to the expanded configuration includes moving the proximal end of the expandable basket axially towards the distal end of the expandable basket to invert the proximal portion of the expandable basket towards the distal portion of the expandable basket to form the proximally oriented cavity.

In certain aspects of the invention, moving the expandable basket from the collapsed configuration to the expanded configuration includes moving the distal end of the expandable basket axially towards the proximal end of the expandable basket to invert the proximal portion of the expandable basket towards the distal portion of the expandable basket to form the proximally oriented cavity. In some embodiments, the proximal end of the expandable basket is spaced radially inward from a peripheral edge of the distal portion of the expandable basket when the proximal portion is inverted towards the distal portion of the expandable basket.

In some aspects of the invention, the method further includes securing axial positions of the proximal and distal ends of the expandable basket relative to each other after forming the proximally oriented cavity to maintain the expandable basket in the expanded configuration. The proximal and distal ends of the expandable basket may be securable relative to each other in a plurality of axial positions such that a shape or size of the proximally oriented cavity is adjustable. In some embodiments, the distal portion of the expandable basket comprises a pre-set conical configuration.

In some aspects of the invention, the method for retrieving a thrombus from a neurovasculature of a patient further includes aspirating a retrieved thrombus from the proximally oriented cavity of the expandable basket out of the patient. In some embodiments, inserting the intravascular device includes positioning the expandable basket distal to the thrombus in the collapsed configuration via a delivery catheter extending around at least a portion of the expandable basket. In some embodiments, the method further includes moving the expandable basket to the collapsed configuration from the expanded configuration for withdrawal from the patient via the delivery catheter after removal of a retrieved thrombus.

In some aspects of the invention, the expandable basket may be retracted proximally toward the aspiration catheter such that at least a portion of the expandable basket cups or surrounds a distal portion of the aspiration catheter. During this retraction, the aspiration catheter may be maintained in a substantially stationary position. In other aspects of the invention, the aspiration catheter may be advanced distally toward the proximally oriented cavity of the expandable basket such that at least a portion of the expandable basket cups or surrounds a distal portion of the aspiration catheter. The expandable basket may be radially expanded to contact a vessel wall distal to the thrombus (or other obstruction) being retrieved, and may effectively create a seal against the vessel wall to prevent emboli from being released distally. This seal may be maintained while the aspiration catheter is advanced all the way up to the dome of the proximally oriented cavity, such that all of the thrombus may be aspirated while preventing emboli from being released distally. During this event, the expandable basket may be maintained in a substantially stationary position. In some aspects of the invention, a portion of the proximally oriented cavity of the expandable basket may come in contact with the distal portion of the aspiration catheter. For example, aspiration catheter may be advanced all the way to the top of the dome formed by the proximally oriented cavity such that the dome of the proximally oriented cavity comes in contact with the distal portion of the aspiration catheter (or alternatively, the expandable basket may be retracted such that the top of the dome of the proximally oriented cavity comes in contact with the distal portion of the aspiration catheter). In some aspects of the invention, a combination of both techniques may be used.

In some aspects of the invention, a thrombus (or some other obstruction) may be capped by surrounding at least a distal portion of the thrombus within the proximally oriented cavity of the expandable basket. The thrombus may be retrieved from a vasculature in conjunction with a catheter proximal to the thrombus so as to remove the thrombus substantially intact.

In some aspects of the invention, the method further includes locking a position of the outer delivery shaft relative to a position of the inner core wire after the proximally oriented cavity is formed to maintain the expandable basket in the expanded configuration during engagement and retrieval of the thrombus. In certain embodiments, the expandable basket is constructed from a radiopaque material. In some embodiments, the intravascular device includes a coil extending around a distal tip of the inner core wire. In certain embodiments, the inner core wire tapers in diameter from a proximal portion to a distal portion of the inner core wire. In certain embodiments, the method further includes filtering into the proximally oriented cavity particulates released during aspiration or removal of the thrombus. In some embodiments, the method further includes withdrawing the expandable basket in the collapsed configuration from the patient via the delivery catheter.

In some aspects of the invention, deploying the expandable basket from the collapsed configuration to the expanded configuration includes moving the expandable basket to a partially expanded configuration between the collapsed configuration and the expanded configuration prior to moving at least one of the proximal end or distal end relative to each other, wherein the expandable basket is not constrained by a delivery catheter or sheath extending around at least a portion of the expandable basket. In some aspects of the invention, the method further includes pivoting the expandable basket so that the expandable basket remains substantially centered in the neurovasculature and substantially maintains vessel opposition during retraction of the expandable basket during thrombus retrieval. In some aspects of the invention, a shape of the proximally oriented cavity is substantially maintained independent of the retraction or retracting step of the expandable basket.

In another aspect of the invention, an intravascular device for filtering particulates released during an intravascular procedure performed upon a patient to prevent distal migration of the released particulates is provided that includes the an outer delivery shaft and an expandable basket movable between a collapsed configuration and an expanded configuration. The expandable basket is configured to be in the collapsed configuration during delivery into a vasculature of the patient and in the expanded configuration to filter particulates released during the intravascular procedure. The expandable basket includes a proximal end and a distal end. The proximal end is configured to be centrally and pivotally coupled to the outer delivery shaft, and at least one of the proximal end or the distal end is movable relative to each other such that a proximal portion of the expandable basket is invertible towards a distal portion of the expandable basket to form a proximally oriented cavity in the expanded configuration configured to retain the released particulates therein.

In another aspect of the invention, a method for filtering particulates released during an neurovascular procedure performed upon a patient to prevent distal migration of the released particulates is provided that includes advancing an neurovascular device into a neurovasculature of the patient. The neurovascular device includes an expandable basket movable between a collapsed configuration and an expanded configuration and includes a proximal end and a distal end. The proximal end is configured to be centrally and pivotally coupled to an outer delivery shaft. The method includes deploying the expandable basket from the collapsed configuration to the expanded configuration by moving at least one of the proximal end or distal end relative to each other to invert a proximal portion of the expandable basket towards a distal portion of the expandable basket to form a proximally oriented cavity. The proximally oriented cavity in the expanded configuration to filter particulates released during the neurovascular procedure. The method further includes capturing the released particulates within the proximally oriented cavity.

In another aspect of the invention, a method for filtering particulates released during a neurovascular aspiration procedure performed upon a patient to prevent distal migration of the released particulates is provided, the method includes advancing a neurovascular device into a neurovasculature of the patient, the neurovascular device comprising an expandable basket movable between a collapsed configuration and an expanded configuration and having a proximal end and a distal end, the proximal end configured to be centrally and pivotally coupled to an outer delivery shaft; anchoring the neurovascular device distal of a thrombus; deploying the expandable basket from the collapsed configuration to the expanded configuration by moving at least one of the proximal end or distal end relative to each other to invert a proximal portion of the expandable basket towards a distal portion of the expandable basket to form a proximally oriented cavity, the proximally oriented cavity in the expanded configuration configured to filter particulates released during the neurovascular aspiration procedure; aspirating the thrombus; and capturing the released particulates of the thrombus within the proximally oriented cavity while aspirating.

In some aspects of the invention, the outward radial force exerted by the expandable basket against the vasculature (e.g., when it is in its expanded configuration) may be sufficient to secure the intravascular device in place without the use of any separate anchors. An outside perimeter of the expandable basket may intimately contact a wall of the vasculature to maintain vessel opposition and fixation of the expandable basket. The anchor position of the intravascular device may be repositioned or adjusted distal of a thrombus by, for example, collapsing or partially collapsing the expandable basket, repositioning the expandable basket, and again expanding the expandable basket. In some aspects of the invention, the anchoring may be carried out without blocking blood flow within the vasculature. In some aspects of the invention, the delivery catheter through which the intravascular device was advanced may be withdrawn, and an aspiration catheter may be navigated to the anchored expandable basket. The anchored expandable basket may provide a substantially fixed pre-positioned guide to the thrombus. The aspiration catheter may be tracked over the outer delivery shaft of the vascular device. Once the aspiration catheter is near an obstruction (e.g., a thrombus), the obstruction may be aspirated as the aspiration catheter is advanced distally toward the expandable basket. During this aspiration, any released particulates of the obstruction may be filtered by the expandable basket and retained within the proximally oriented cavity. In some aspects of the invention, separate anchors may be included to secure the intravascular device (e.g., the expandable basket) in position within a vasculature (e.g., a neurovascular).

In some aspects of the invention, the expandable basket may be constructed from a radiopaque material. The intravascular device may include a radiopaque marker band coupled to an inner perimeter of the outer delivery shaft and further coupled to a proximal anchoring element that is coupled to the proximal end of the expandable basket. In some aspects of the invention, the expandable basket may be constructed from a radiopaque material, and the coil may be radiopaque. The intravascular device may further include a radiopaque proximal anchoring element (e.g., a coil) at the proximal end of the expandable basket, and a radiopaque distal anchoring element (e.g., a coil) at the distal end of the expandable basket. The intravascular device may also include a radiopaque supporting coil between the proximal anchoring element and the distal anchoring element.

In some aspects of the invention, an intravascular device kit for retrieving an obstruction from a patient is provided. The kit may include an intravascular device, such as the one disclosed herein, and an extender wire disposed within a packaging container. The intravascular device may include an outer delivery shaft and an expandable basket movable between a collapsed configuration and an expanded configuration. The extender wire may be releasably coupleable to the intravascular device. In some aspects of the invention, the intravascular device and the extender wire may be disposed together within the packaging container to form an interleaved coil. The expandable basket may be configured to be in the collapsed configuration during delivery into a vasculature of the patient and in the expanded configuration during engagement and retrieval of the obstruction. The expandable basket may include a proximal end and a distal end. At least one of the proximal end or the distal end may be movable relative to each other such that a proximal portion of the expandable basket is invertible towards a distal portion of the expandable basket to form a proximally oriented cavity in the expanded configuration configured to engage and retrieve an obstruction. The proximal end of the expandable basket may be configured to be centrally and pivotally coupled to the outer delivery shaft. In some aspects of the invention, the kit may include one or more extender hypotubes for coupling the extender wire to the intravascular device. In some aspects of the invention, the kit may include a delivery catheter disposed within the packaging container. The delivery catheter may be disposed in a coil interleaved with the intravascular device and the extender wire.

BRIEF DESCRIPTION OF THE DRAWINGS

FIG. 1I-FIG. 1J are illustrations of the expandable basket of FIG. 1A in a partially expanded configuration and an expanded configuration, respectively, with multiple braid layers in accordance with aspects of the invention.

FIG. 1K is an illustration of the expandable basket of FIG. 1A in an expanded configuration with multiple layers in accordance with other aspects of the invention.

FIG. 2A-FIG. 2E are a series of views illustrating an exemplary intravascular procedure or process including insertion and removal of the intravascular device of FIG. 1A-FIG. 1B in accordance with aspects of the invention.

FIG. 3A-FIG. 3B illustrate exemplary intravascular procedures or processes of the intravascular device of FIG. 1A-FIG. 1B in accordance with other aspects of the invention.

FIG. 4A-FIG. 4B illustrate another exemplary intravascular procedure or process of the intravascular device of FIG. 1A-FIG. 1B in accordance with other aspects of the invention.

FIG. 6A-FIG. 6J illustrate example embodiments where the expandable basket of the intravascular device 100 is used as a filter to aid the aspiration of an obstruction.

FIG. 8A-FIG. 8C illustrate an example embodiment of an extender wire that is configured to releasably couple to the intravascular device FIG. 9A-FIG. 9F illustrate an example embodiment where the expandable basket is used to retrieve a foreign object other than a thrombus or some other naturally occurring obstruction.

FIG. 12 is a flowchart illustrating an example method for filtering at least one particulate in a vasculature of a patient with an embodiment of the intravascular device described herein, where the particulate may be released during a procedure performed upon a patient.

DETAILED DESCRIPTION OF THE INVENTION

Figure 1A:
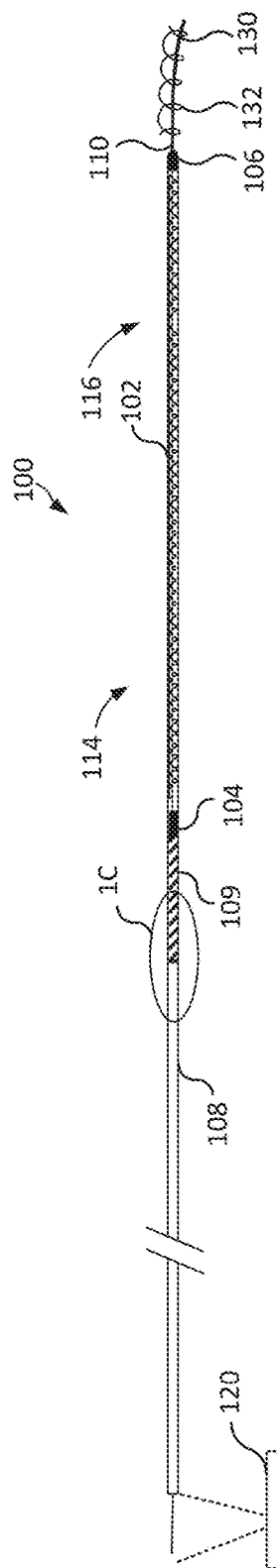
FIG. 1A and FIG. 1B are illustrations of an intravascular device with an expandable basket in the collapsed and expanded configurations, respectively, in accordance with aspects of the invention.

With reference to FIG. 1A-FIG. 6, embodiments of an intravascular device 100 for engaging, retrieving, capturing, filtering, or removing an obstruction are illustrated. As used herein, the term "obstruction" includes, but is not limited to, a thrombus, embolus, clot, or other particulate. The intravascular device 100 may additionally, or instead, be configured to provide protection from distal emboli or other obstructions (e.g., as a filtering device) during removal or aspiration of the obstruction or another intravascular procedure (e.g., to remove, dissolve, or break up the obstruction). The intravascular device 100 includes an expandable basket 102 movable between a collapsed configuration (FIG. 1A) and an expanded configuration (FIG. 1B). The expandable basket 102 is configured to be in the collapsed configuration during delivery or insertion into a vasculature (e.g., a neurovasculature) of the patient and in the expanded configuration during engagement and retrieval or filtering of the obstruction as described in more detail below with reference to FIG. 2A-FIG. 2E.

The expandable basket 102 includes a proximal end 104 and a distal end 106. The proximal end 104 is centrally and pivotally coupled to an outer delivery shaft 108 (e.g., a hypotube) allowing the expandable basket 102 to pivot and maintain contact with a vessel wall as described in more detail below with reference to FIG. 5. The distal end 106 is coupled to an inner wire 110 (e.g., an actuating wire, core wire, delivery wire) extending coaxially through the outer delivery shaft 108. At least one of the proximal end 104 or the distal end 106 is movable relative to each other such that a proximal portion 114 of the expandable basket 102 is invertible into or towards a distal portion 116 of the expandable basket 102 to form a proximally oriented cavity 112 in the expanded configuration.

The proximally oriented cavity 112 includes a cavity 118 (e.g., opening, basin, catch portion) configured to engage, capture, retrieve, or filter a clot or other obstruction therein for removal from a patient during an intravascular procedure as described herein. As illustrated in FIG. 1B, the proximally oriented cavity 112 may have a parabolic-shaped cavity 118 formed by the inverted proximal portion 114 of the expandable basket 102. A vertex or apex 124 of the cavity 118 may be pivotally and centrally coupled to the outer delivery shaft 108. As such, in the expanded configuration, the outer delivery shaft 108 is coupled to the expandable basket 102 at a location or position (e.g., pivoting point) spaced apart (e.g., radially inward) from a peripheral edge or lip 126 of the distal portion 116 extending circumferentially around the proximally oriented cavity 112. In some embodiments, the proximally oriented cavity may have a cup-shaped cavity.

In some embodiments, the proximal end 104 is movable relative to the distal end 106 of the expandable basket 102 to form the proximally oriented cavity 112. For example, the outer delivery shaft 108 having a distal portion or end pivotally coupled to the proximal end 104 of the expandable basket 102 may be moved (e.g., pushed) distally to invert the proximal portion 114 of the expandable basket 102 towards the distal portion 116. In other embodiments, the distal end 106 is movable relative to the proximal end 104 of the expandable basket 102 to form the proximally oriented cavity 112. For example, the inner wire 110 having a distal portion coupled to the distal end 106 of the expandable basket 102 may be moved (e.g., pulled, drawn) proximally to invert the proximal portion 114 of the expandable basket 102 towards the distal portion 116. In yet other embodiments, both the proximal end 104 and the distal end 106 of the expandable basket 102 are movable relative to each other to move the expandable basket 102 to the expanded configuration and form the proximally oriented cavity 112.

The intravascular device may include a handle 120 (e.g., a catheter handle) coupled to the outer delivery shaft 108 or inner wire 110. The handle 120 may include one or more actuating components 128 configured to move the proximal end 104 or the distal end 106 of the expandable basket 102 relative to each other (e.g., by pushing the outer delivery shaft 108 distally or drawing the inner wire 110 proximally). The components 128 may also be configured to move a delivery catheter as discussed in more detail below. As discussed above, the relative movement of the proximal end 104 or distal end 106 moves the expandable basket 102 from the collapsed configuration to the expanded configuration. Such relative movement compresses the expandable basket 102 longitudinally or axially and inverts the proximal portion 114 of the expandable basket 102 towards the distal portion 116 to form the proximally oriented cavity 112.

The handle 120 may include one or more locking mechanisms 122 configured to lock or secure a location or position of the outer delivery shaft 108 and the inner wire 110 relative to each other (e.g., relative positions of the proximal and distal ends of the expandable basket 102). By securing the relative positions of the outer delivery shaft 108 and inner wire 110, the expandable basket 102 may be maintained in the expanded configuration after the proximally oriented cavity 112 is formed (e.g., independent of pulling force when engaging and retrieving an obstruction). Maintaining the expandable basket 102 in the expanded configuration prevents or reduces compression of the expandable basket 102 as the expandable basket 102 is pulled across or over an obstruction that may be, for example, strongly adhered to a vessel wall.

Further, in some embodiments, relative positions of the proximal and distal ends of the expandable basket 102 may be configured to be secured in multiple or various positions (e.g., two or more positions relative to each other). For example, the locking mechanism 122 may be configured to secure the outer delivery shaft 108 and the inner wire 110 relative to each other at multiple positions. A shape or size of the proximally oriented cavity 112 may be modified depending on the distance between positions of the outer delivery shaft 108 and inner wire 110. In some embodiments, the outer delivery shaft 108 may be secured at a first position or first distance relative to the inner wire 110 with the proximally oriented cavity 112 having a first diameter and a first length. The outer delivery shaft 108 may then be secured at a second position or second distance relative to the inner wire 110 (e.g., with the proximal end 104 more proximal or farther away from the distal end 106 than in the first position). The second distance may be greater than the first distance. In the second position, the proximally oriented cavity 112 may have a second diameter less than the first diameter or a second length greater than the first length. In other embodiments, the second distance may be less than the first distance (e.g., with the proximal end 104 more distal or closer to the distal end 106). Such adjustability may allow a clinician to change the shape or size of the proximally oriented cavity 112 as desired to engage and retrieve or filter obstructions in different sized vessels or during a same intravascular procedure.

Figure 1B:
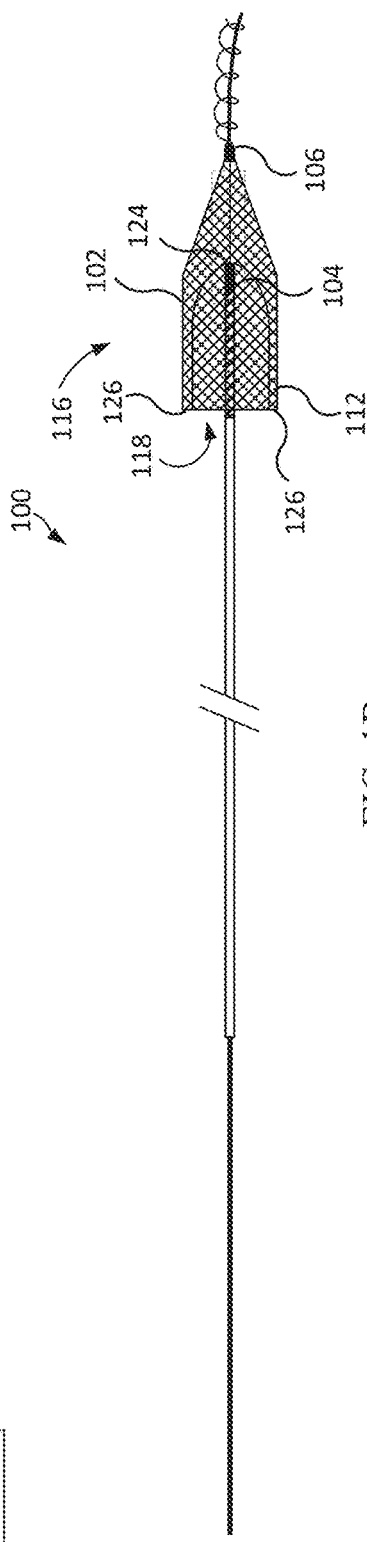

As illustrated in FIG. 1A-FIG. 1B, the expandable basket 102 may be constructed from a braided or mesh material (e.g., nitinol, nanofiber, polymer, or other suitable material). For example, the expandable basket 102 may be constructed from a wire mesh, braid, woven material, matrix, or sheet with laser-cut holes. In particular, the basket 102 may be made of a metallic material (e.g., nitinol, cobalt chromium, platinum tungsten, DFT wire including nitinol/platinum tubes) to provide structural integrity for maintaining the basket 102 in an inverted configuration (e.g., during a thrombectomy procedure) as described herein. A density of the braided material may be varied. For example, pore density of the braid may be denser in some portions of the basket 102 relative to other portions (e.g., middle of the basket 102 relative to end or peripheral portions). The pore density may be different or varied for different applications (e.g., filtering, stopper, thrombectomy) or different sized obstructions. In some embodiments, the expandable basket 102 is made from or includes a radiopaque material which may allow a clinician to see or identify whether the expandable basket 102 is in the collapsed or expanded configuration or to aid in properly positioning the expandable basket 102 (e.g., distal of an obstruction). In some embodiments, the proximal or distal ends of the expandable basket 102 may have pre-set (e.g., heat-set) cylindrically-shaped or conical-shaped configurations, respectively as discussed in more detail below. In other embodiments, the proximal or distal ends may have other suitably-shaped pre-set configurations. The expandable basket 102 may be made from a porous material or fabric. The expandable basket 102 may be configured (e.g., include pores sized) to filter or trap (e.g., retain) released particulates or a captured obstruction therein while allowing blood flow therethrough. Particulates released distally may be problematic, because they may, for example, coalesce and form emboli within the vasculature, and may thereafter obstruct blood flow. Clinical studies have consistently shown that preventing particulates from being released distally during procedures performed near obstructions in the vasculature significantly improves patient outcomes by, for example, reducing the risk of procedural complications resulting from emboli formation by the released particulates. By employing a filtering or trapping mechanism, the risk of emboli formation from these procedures is significantly reduced, resulting in improved immediate and long-term patient health. The expandable basket 102 may be sized to fit in vessels with diameters from 2 mm to 9 mm, 2.5 mm to 8 mm, 2.5 mm to 5 mm, 2.5 mm to 3 mm, and/or any value therebetween. For example, the basket 102 may be sized such that in the expanded configuration, outer walls or periphery of the basket 102 expand until they resile against inner walls of the vessel to secure the basket 102 in position with no or minimal gaps between the basket 102 and inner walls of the vessel. In some embodiments, the expandable basket 102 may be sized such that when it is inverted, the resulting diameter is suitably larger than the diameter of the vessel, so that, for example, it can exert sufficient outward radial force to be secured within the vessel. For example, the expandable basket 102 may have an inverted diameter of 2 mm when it is to be secured to a 1 mm vessel. When the vessel is in the neurovasculature, it may be particularly advantageous to size the expandable basket 102 to have an inverted diameter of between 2 mm to 6 mm. In some embodiments, the expandable basket 102 to have an inverted diameter of between 30 mm to 40 mm, particularly for uses outside the neurovasculature. For example, such a range may be suitable for aortic valve replacement procedures. The disclosure also contemplates use of the invention in procedures where the release of emboli distally is possible, as may be the case, for example, with pulmonary embolism procedures, stenting procedures (e.g., carotid stenting), aortic valve replacement procedures, etc. In some embodiments, anchors may be included to secure the basket 102 in position. In other embodiments, the outward radial force exerted by the expandable basket 102 may be sufficient to secure the expandable basket 102 in place, without any anchors.

Figure 1C:
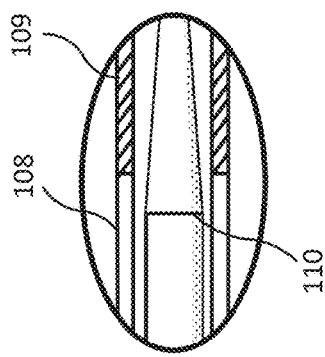
FIG. 1C is a detailed section view of a portion of the intravascular device of FIG. 1A.
Figure 1F:
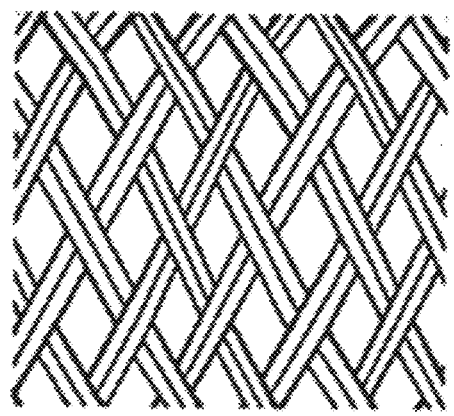
FIG. 1D-FIG. 1F are illustrations of exemplary braid patterns of the expandable basket of FIG. 1A-FIG. 1B in accordance with aspects of the invention.
Figure 1E:
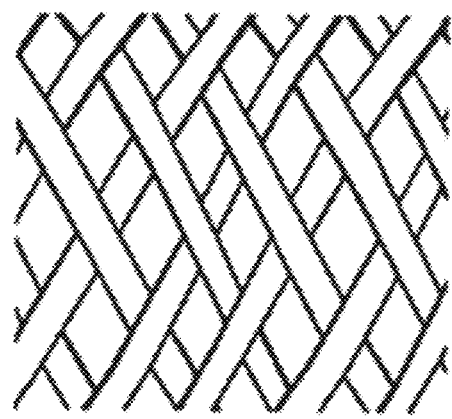
Figure 1D:
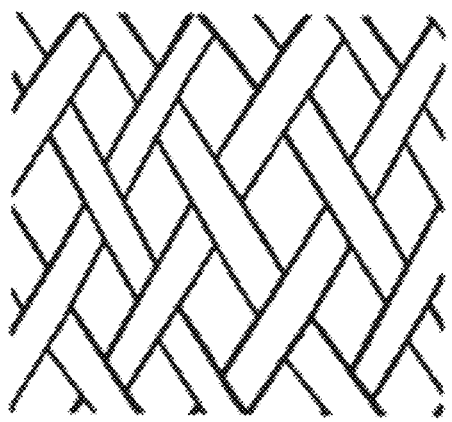

FIG. 1D-FIG. 1F illustrate exemplary mesh or braid patterns for the basket 102. As discussed above, the wire mesh or braid may include a plurality of woven, braided, or criss-crossed wires. As illustrated in FIG. 1D, in some embodiments, the pattern may include a plurality of wires that are interwoven such that a wire extends over one wire and then under one wire in a repeating pattern. In other embodiments, as illustrated in FIG. 1E, the plurality of wires are interwoven such that a wire extends over two wires and then under two wires in a repeating pattern. In yet further embodiments, as illustrated in FIG. 1F, the plurality of wires are interwoven such that two wires extend over two other wires and then under two other wires in a repeating pattern. In still further embodiments, the wires may be interwoven such that two wires extend over one wire and then under one wire in a repeating pattern.

As discussed above, the expandable basket 102 is pivotally and centrally coupled to a distal end of the outer delivery shaft 108. The outer delivery shaft 108 is a hollow structure or includes a lumen configured to allow the inner wire 110 to extend therethrough. The outer delivery shaft 108 may be constructed out of a metallic material (e.g., stainless steel), multi-layer composite, or other suitable material. In some embodiments, the outer delivery shaft 108 may be made of a same material (e.g., braided) as the expandable basket 102. A distal segment or portion 109 of the outer delivery shaft 108 proximate or at the proximal end of the expandable basket 102 may be more flexible relative to a proximal segment or portion to allow the delivery shaft 108 to bend or pivot relative to the expandable basket 102. In some embodiments, the outer delivery shaft 108 may be a hypotube. The outer delivery shaft 108 may be slotted, spiral or diagonal cut, or include other suitable patterns or shaped notches or holes at the distal segment or portion 109 to allow the distal segment or portion to bend, pivot, or elastically deform relative to the proximal segment or portion. For example, the distal portion 109 may be slotted while the proximal portion of the shaft 108 is unslotted. In other embodiments, the distal portion 109 may include more slots or a higher slot density relative to the proximal portion of shaft 108. In yet further embodiments, relative amount or slot density may vary across the length of the distal portion 109 (e.g., distal half having more slots relative to a proximal half). In some embodiments, instead of or in addition to slots, the distal segment or portion 109 may be made of a different material (e.g., less stiff or more deformable or flexible) relative to the proximal segment or portion of the outer delivery shaft 108. In some embodiments, material stiffness may vary across a length of the distal portion 109.

The inner wire 110 may be a movable or actuatable core or pull wire extending past or distal to the distal end of the outer delivery shaft 108 coupled to the distal end of the expandable basket 102. The inner wire 110 may be constructed out of solid wire(s) or multi-strands of cable twisted together. In some embodiments, a distal tip 130 of the inner wire 110 extends past the distal end 106 of the expandable basket. The distal tip 130 may be an atraumatic tip. In some embodiments, the distal tip 130 includes a protective coil 132 (e.g., a helical coil) extending around the tip 130 configured to resile or deflect against vessel walls such that the expandable basket 102 does not substantially damage or penetrate such walls during delivery to a retrieval or filtering site. The coil 132 may be separate from the inner wire 110 or may be integrated with the inner wire 110. The coil 132 may be coupled to or supported by a portion of the distal tip 130. The coil 132 may be a coil made of platinum, or any other suitable material.

With reference to FIG. 1C, in some embodiments, the inner wire 110 has a smaller diameter at a distal end or portion relative to a proximal end or portion. For example, the inner wire 110 may taper down in diameter from near or proximate to where the outer delivery shaft 108 is coupled to the proximal end 104 of the expandable basket 102 to the distal end 106 of the expandable basket 102. Decreasing or tapering the diameter of the inner wire 110 enhances flexibility for bending or pivoting of the inner wire 110 at the distal portion of the inner wire 110 while providing sufficient stiffness at the proximal portion of the inner wire 110. The proximal portion of the inner wire 110 requires sufficient stiffness to allow application of a push-pull force upon the inner wire 110 to expand the basket 102 or for retrieval of the basket 102. Tapering from a larger diameter to a smaller diameter along a length of the inner wire 110 allows the inner wire 110 to have a larger diameter along a proximal end or portion of the inner wire 110 relative to the distal end or portion. Additionally, a smaller diameter at a distal end or portion of the inner wire 110 may provide increased clearance between an outer diameter of the inner wire 110 and an inner diameter of the outer delivery shaft 108 to reduce friction between the components during actuation of the expandable basket 102. Further, the inner wire 110 may have a coating (e.g., a PTFE coating) to allow it to slide or move more easily (e.g., reduce friction) relative to the outer delivery shaft 108. In some embodiments, the inner wire 110 may be flattened at or near the distal end of the inner wire 110 (for example, the portion of the inner wire distal to the expandable basket 102). In some embodiments, the inner wire 110 may be cylindrical until the flattened portion—i.e., it may have a cylindrical portion and a flattened portion. By flattening the inner wire 110, the distal end of the inner wire one may be made more flexible and easy to deflect, and may consequently facilitate navigation through pathways that may have tight turns requiring increased maneuverability.

Figure 1G:
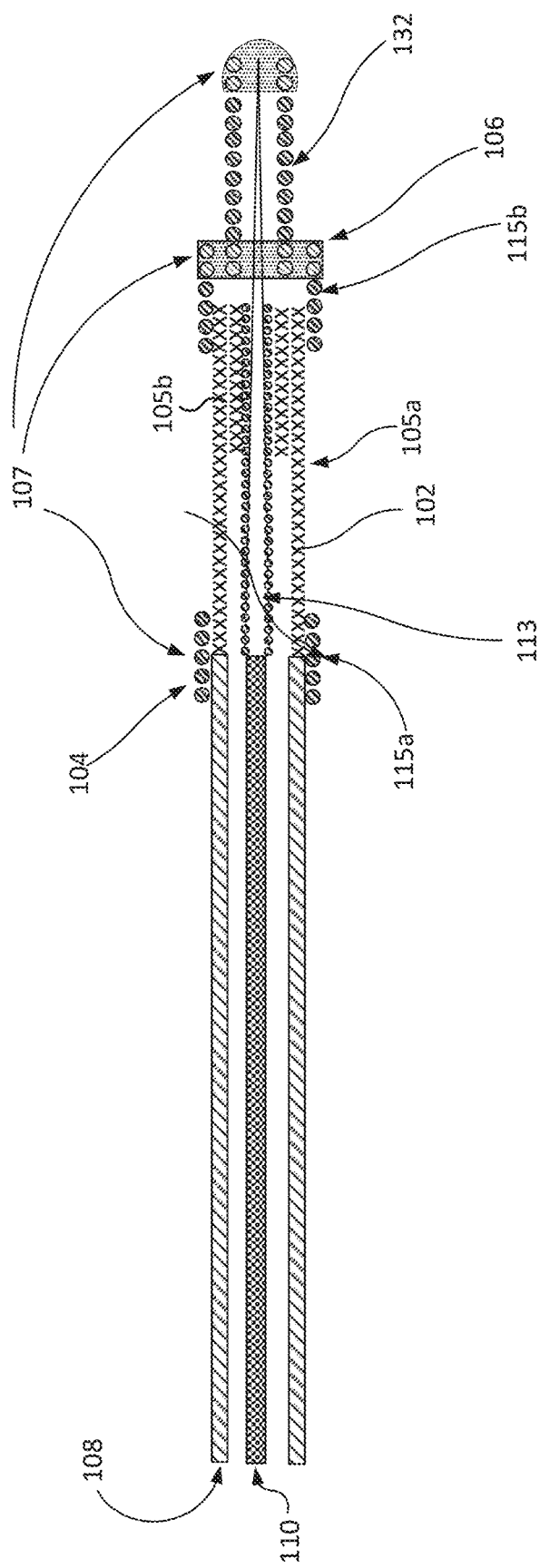
FIG. 1G-FIG. 1H are cross-sectional views of the intravascular device of FIG. 1A-FIG. 1B in accordance with aspects of the invention.
Figure 1H:
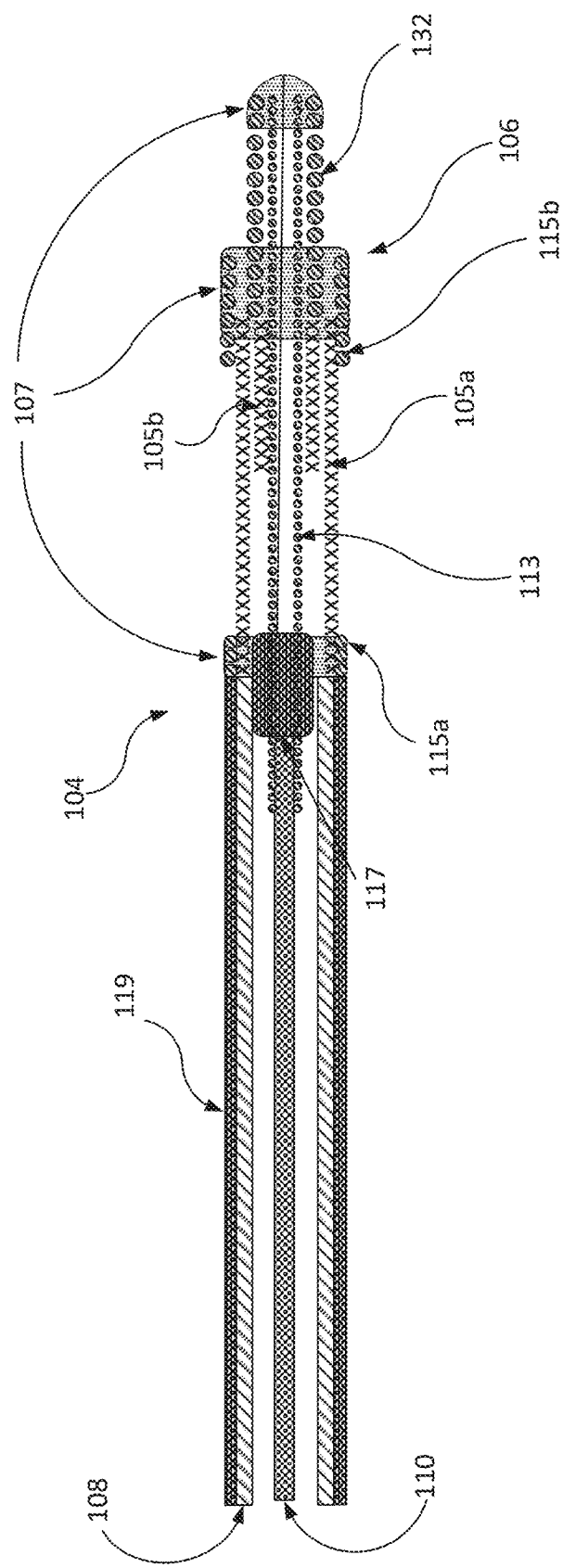

FIGS. 1G-1H illustrate cross section views of the intravascular device 100 of FIG. 1A-FIG. 1B in accordance with embodiments of the present invention. As illustrated in FIG. 1G, the expandable basket 102 is in the collapsed configuration. The expandable basket 102 may include multiple braids or layers (e.g., an outer layer or braid 105a and an inner layer or braid 105b) as described in more detail below with respect to FIG. 1I-FIG. 1K. As described above, proximal and distal ends 104, 106 of the basket 102 may be coupled with the outer delivery shaft 108 and inner wire 110, respectively. Further, the proximal and distal ends of the expandable basket 102 may include proximal and distal anchoring or support components 115a, 115b (e.g., coils). In some embodiments, the basket 102 may be soldered or otherwise coupled to the outer delivery shaft 108 and inner wire 110 at junctions or joints 107. The proximal end 104 of basket 102 is coupled (e.g., generally flush) to or around an outer diameter or perimeter of outer delivery shaft 108. Further, as discussed above, the inner wire 110 may include the coil 132 extending around the distal tip 130. The coil 132 may also be soldered or otherwise coupled to the distal tip 130 of the inner wire at a junction or joint 107. The inner wire 110 may also include a coil 113 around a distal segment or portion of the inner wire 110 (e.g., portion extending through basket 102). The coil 113 may provide strain relief or structural integrity to the wire 110 (e.g., to prevent or reduce potential kinking) such that the basket 102 may be maintained in an inverted configuration.

FIG. 1H illustrates a cross section view of intravascular device 100 in accordance with another embodiment. In such embodiments, the device 100 may include one or more of any of the features described above with respect to FIG. 1G. As illustrated, the device 100 may include a radiopaque marker band 117 coupled (e.g., soldered) to an inner diameter or perimeter of the outer delivery shaft 108. This may aid in positioning the intravascular device 100 or identifying (e.g., to a clinician) when the basket 102 is in an expanded configuration (e.g., inverted configuration). The marker band 117 may be provided in addition to or instead of constructing the basket 102 out of a radiopaque material. The proximal end 104 of the inner wire 110 may be coupled to the marker band 117 such that the inner wire 110 does not extend around or is not coupled to an outer diameter of the outer delivery shaft 108. Coupling the proximal end 104 of the inner wire 110 to the marker band 117 in this manner reduces the profile of the basket 102 in the collapsed configuration relative to a profile in which the proximal end 104 is coupled to the outer diameter of the delivery shaft 108. The outer delivery shaft 108 may also include an outer sheath or coating 119 (e.g., made of PTFE) to reduce friction when positioning or moving the shaft 108. In some embodiments, the outer delivery shaft 108 may also include a thin jacket that may provide lubricity and/or prevent fluid from passing through.

In some embodiments, the proximal or distal portions 114 or 116 of the expandable basket 102 may have pre-set (e.g., heat-set, shape-set, heat treated) cylindrically-shaped or conically-shaped configurations, respectively. For example, the proximal and distal portions 114 or 116 may be made of shape-memory materials pre-set into different configurations such that only one of the proximal or distal portions (e.g., the proximal portion) is invertible to form the proximally oriented cavity 112. In other embodiments, the proximal or distal portions 114 or 116 may have other suitably-shaped pre-set configurations. In some embodiments, the distal portion 116 has a different pre-set configuration than the proximal portion 114 to allow only the proximal portion of the expandable basket 102 to invert or be invertible. For example, in some embodiments, the distal portion 116 may have a conical-shaped pre-set configuration and the proximal portion may have a more cylindrically-shaped configuration (e.g., proximally oriented cavity 112). As one of the proximal or distal ends of the expandable basket 102 is moved toward each other, the proximal portion 114 may invert to return to the pre-set cylindrical shaped configuration while the distal portion 116 will remain or tend to remain in the pre-set conical-shaped configuration (FIG. 1B).

With reference to FIG. 1I-FIG. 1K, portions of the expandable basket 102 may include multiple layers or braids (e.g., two or more layers or braids). Portions of the expandable basket 102 that are not configured to be inverted or invertible (e.g., distal portion) may include more layers or braids relative to portions of the expandable basket 102 that are configured to be inverted or invertible (e.g, proximal portion). For example, a portion that is not configured to be inverted or invertible (e.g., the distal portion) may include two layers, while a portion that is configured to be inverted or invertible (e.g., the proximal portion) may include only one layer. Having additional layers on one portion (e.g., the distal portion 116) may provide increased stiffness to that portion, which may allow that portion to have additional resistance to inverting. The multiple layers may also provide increased pore density (e.g., for improved filtering of smaller particulates). Configuring the expandable basket 102 in this manner may allow only the proximal portion 114 (e.g., or portion without multiple layers or with less layers) of the expandable basket 102 to invert or be invertible while the distal portion 116 (e.g., portion with multiple layers or with more layers) is maintained in a non-inverted position when the expandable basket 102 is moved to the expanded configuration from the collapsed configuration. This provides selective inversion of the expandable basket 102 in forming the proximally oriented cavity 112. As illustrated, in some embodiments, the expandable basket 102 includes an outer braid or layer 105*a* extending from the proximal portion to the distal portion. The expandable basket 102 includes an inner braid or layer 105*b* extending only along the distal portion of the basket. Therefore, the proximal portion 114 includes one less layer or braid relative to the distal portion 116. The expandable basket 102 may include one or more inner layers 105*b* along a portion of the basket (e.g., distal portion 116). The inner layer or braid 105*b* may extend along at least or up to ¾, ⅔, ½, ⅓, ¼, or any value therebetween of the length of the basket 102. For example, the inner layer or braid 105*b* may extend along at least or up to one half of the length of the basket 102 (e.g., a distal half of the basket) or at least or up to one third of the length of the basket 102 (e.g., a distal third of the basket). As a length of the basket 102 with multiple layers or braids (e.g., the inner layer 105*b*) increases (FIG. 1K), the potential depth or length of the proximal oriented cavity 112 is increased relative to a basket 102 with shorter length multiple layers or braids (FIG. 1J). As illustrated in FIG. 1J or FIG. 1K, in some embodiments, the proximal portion 114 may be inverted towards the distal portion 116 to form the proximally oriented cavity 112 such that the cavity 112 extends at least partially within the inner layer 105 of the non-inverted distal portion of the basket 102. In this manner, the cavity 112 is formed with multiple layers or walls (e.g., three layers outer layer, inner layer, and inverted portion or layer). In some embodiments, when the expandable basket 120 is inverted, the resulting configuration may serve as a filter having a total number of layers that is the sum of the portion that is not configured to be inverted or invertible and the portion that is configured to be inverted or invertible. For example, if there are two layers in the former and one layer in the latter, the expandable basket 102 may serve as a filter having three layers when it is inverted.

In some embodiments, the inner layer 105*b* is configured to expand or expands more or equivalently relative to the outer layer 105*a* when the basket 102 is moved to a partially expanded or intermediary configuration from the collapsed configuration as described in more detail below (FIG. 2A-FIG. 2E). For example, the inner layer 105*b* may be made from a more resilient or elastic material relative to the outer layer 105*a*. In other embodiments, the inner layer 105*b* may be heat-set or pre-set to a larger or equivalent diameter configuration relative to the outer layer 105*a*. By doing so, when the basket 102 is moved to the intermediary (e.g., partially) expanded or the expanded configuration, space or gaps between the inner and outer layers is reduced or minimized to keep the inner layer intimately opposed to or with the outer layer in the partially or fully expanded configurations. This may provide a better defined opening or space for the invertible (e.g., proximal) portion of the basket (e.g., with only an outer layer) to invert into as described herein. This may result in an improved or more well defined opening, configuration, or shape of basket 102 (e.g., more cylindrical or conical shape) or proximally oriented cavity in the expanded configuration.

Figure 1L:
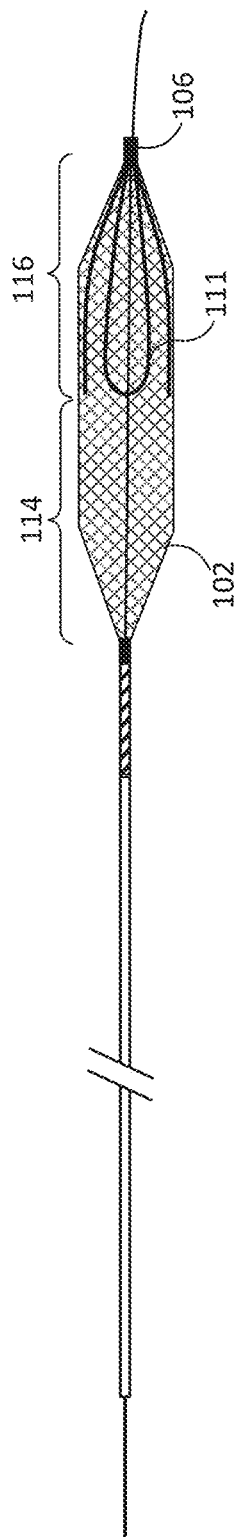
FIG. 1L-FIG. 1M are illustrations of the expandable basket of FIG. 1A in a partially expanded configuration and an expanded configuration, respectively, with support ribs in accordance with aspects of the invention.
Figure 1M:
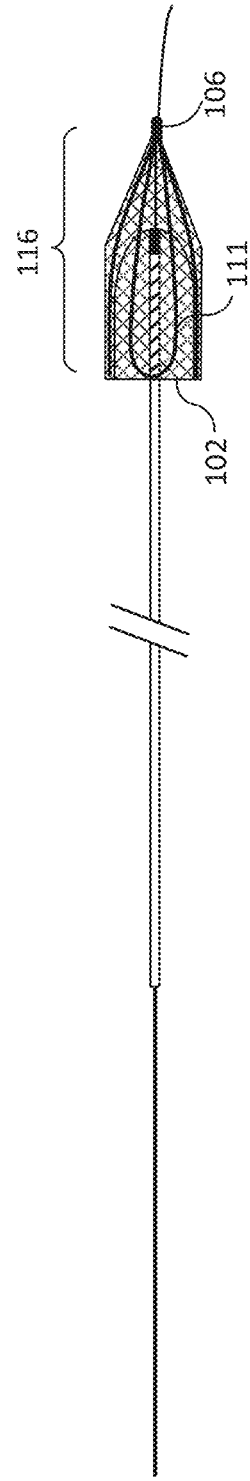
Figure 1N:
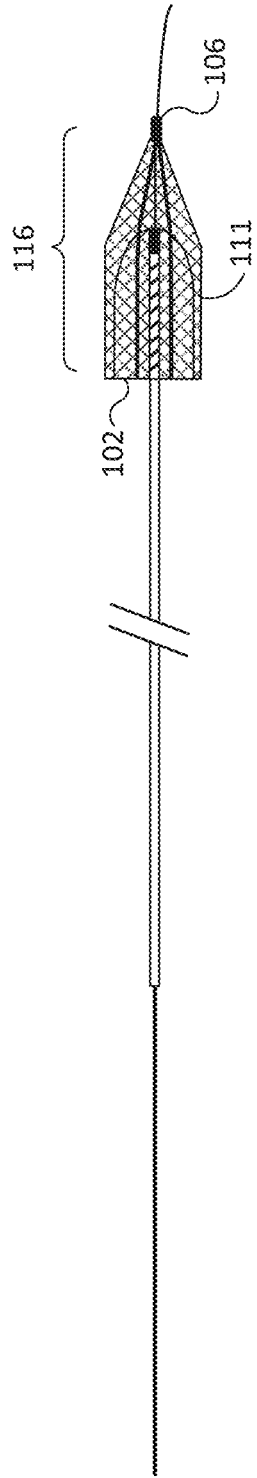
FIG. 1N is an illustration of the expandable basket of FIG. 1A in an expanded configuration with support ribs in accordance with other aspects of the invention.

With reference to FIG. 1L-FIG. 1N, the expandable basket 102 may include one or more support spines or ribs 111 extending longitudinally along an inner surface or side of the distal portion 116 of the expandable basket 102. The proximal portion 114 may be configured without the support spines or ribs 111. The support spines or ribs 111 provide increased stiffness or resistance to inverting in the distal portion 116. Configuring the expandable basket with the support spines or ribs 111 in this manner may allow only the proximal portion 114 of the expandable basket 102 to invert or be invertible while the distal portion 116 is maintained in a non-inverted position by the support spines or ribs 111 when the expandable basket 102 is moved to the expanded configuration from the collapsed configuration. The support spines or ribs 111 may have proximal and distal ends. The distal ends may be coupled to or extend from the distal end 106 of the expandable basket 102 and the proximal ends may be positioned at or proximate a proximate end of the distal portion 116 of the expandable basket 102. The support spines or ribs 111 may have a circular or looped configuration (FIG. 1L-FIG. 1M). In other embodiments, the support spines or ribs 111 may have substantially linear or straight configurations (FIG. 1N). In yet other embodiments, the support spines or ribs 11 may have both linear and looped support ribs 111 or other suitably-shaped ribs. In further embodiments, the proximal and distal portions 114 and 116 may be constructed of materials with different stiffness or pore density (e.g., with or without support ribs 111) to allow only the proximal portion 114 to be invertible. For example, the distal portion 116 may be constructed with a material greater in stiffness or pore density than the proximal portion 114.

FIG. 2A-FIG. 2E, illustrate a series of views of an exemplary intravascular procedure or process including insertion and removal of the intravascular device 100. In some embodiments, the intravascular device 100 may be delivered into the patient's vasculature 246 (e.g., lumen, blood vessel, neurovasculature) via a delivery catheter or sheath 240 coupled to the catheter handle 120. The delivery catheter 240 is configured to extend around at least a portion of the outer delivery shaft 108 and the expandable basket 102. During delivery, in some embodiments, the delivery catheter 240 may be inserted (e.g., distally in a direction identified by arrow D) through a patient's vasculature and an obstruction 242. A distal tip of the delivery catheter 240 may be positioned at or distal to a distal end of the obstruction 242 (FIG. 2A) forming a channel as it extends or passes through the obstruction 242. In some embodiments, the expandable basket 102 is carried into position by the delivery catheter in the collapsed configuration as the delivery catheter 240 is inserted into position. In other embodiments, the expandable basket 102 is inserted into position through the delivery catheter 240 in the collapsed configuration after a distal tip of the delivery catheter 240 is positioned at or distal to a distal end of the obstruction 242.

As illustrated in FIG. 2B, the delivery catheter 240 may then be retracted or withdrawn (e.g., pulled back in a proximal direction identified by arrow P) to expose or reveal the expandable basket 102. In some embodiments, the expandable basket 102 may be inserted distally through and past the tip of the delivery catheter 240 into position in the vasculature 246 prior to or while the delivery catheter 240 is being withdrawn. Once the delivery catheter 240 is withdrawn (e.g., force maintaining the expandable basket 102 in the collapsed configuration is withdrawn), the expandable basket 102 expands (e.g., slightly) due to an expansive force (e.g., elastically deformable members, shape-memory) of the expandable basket 102. The proximal and distal ends of the expandable basket 102 move towards each other (e.g., longitudinally compressing the basket 102) as the catheter 240 is withdrawn. The expandable basket 102 is in an intermediary configuration (e.g., a partially expanded configuration) between the collapsed configuration and the expanded configuration.

With reference to FIG. 2C and as discussed above, the expandable basket 102 may then be moved to the expanded configuration such that a proximal portion 114 of the expandable basket 102 is inverted towards the distal portion 116 of the expandable basket 102 to form the proximally oriented cavity 112 with the proximally oriented cavity 118. In some embodiments, the outer delivery shaft 108 may be moved (e.g., pushed) distally to invert the proximal portion 114 of the expandable basket 102 towards the distal portion 116. In addition to, or instead of moving the outer delivery shaft 108, the inner wire 110 may be moved (e.g., pulled, drawn) proximally to invert the proximal portion 114 of the expandable basket 102 towards the distal portion 116. Relative locations or positions of the inner wire 110 and outer delivery shaft 108 may then be secured or locked as described above (e.g., with handle locking mechanisms 122) to maintain the expandable basket 102 in the expanded configuration (e.g., independent of retraction of the basket as described in more detail below). The expandable basket 102 is pivotally and centrally coupled to a distal end of the outer delivery shaft 108.

As illustrated in FIG. 2D, the expandable basket 102 in the expanded configuration may then be pulled (e.g., retracted) or drawn proximally through the obstruction 242. For example, the inner wire 110 or the outer delivery shaft 108 may be drawn proximally (e.g., via the handle 120) to engage and retrieve the obstruction 242 into the proximally oriented cavity 112 of the expandable basket 102. As discussed above, the proximally oriented cavity 112 may be used to filter released particulates (e.g., of the obstruction during obstruction removal or retrieval) in addition to or instead of retrieving an obstruction 242. Once the obstruction 242 is retrieved (e.g., or particulates filtered) into the proximally oriented cavity 112, an aspiration sheath or catheter 244 (e.g., the delivery catheter 240 or a separate catheter) may then be positioned proximate the expandable basket 102. In some embodiments, the aspiration catheter 244 is positioned proximate the expandable basket 102 prior to engagement of the obstruction or filtering of particulates. In some embodiments, aspiration may occur while the expandable basket 102 is drawn proximally to engage or retrieve the obstruction 242. Aspiration may occur prior to, during, or after retrieval of an obstruction or filtering of particulates.

As illustrated in FIG. 2E, the obstruction 242 or other particulates may be aspirated out of the patient via the catheter 244. For example, an aspiration source 245 (e.g., syringe or pump) may be coupled to the catheter 244 to aspirate the obstruction out of the patient. The catheter 244 may include one or more intraluminal aspiration lumens. Aspiration may occur while the catheter 244 is positioned proximate to the expandable basket 102 or while the expandable basket 102 is retrieved or withdrawn. The expandable basket 102 may then be moved to the collapsed configuration after removing the obstruction 242 or portions of the obstruction 242 therefrom (e.g., by unlocking the outer delivery shaft 108 or inner wire 110 and moving the outer delivery shaft 108 proximally or the inner wire 110 distally). The expandable basket 102 may then be drawn proximally through the catheter 244 or another catheter (e.g., the delivery catheter 240) positioned over the outer delivery shaft 108 and inner wire 110 and withdrawn from the patient. In other embodiments, the expandable basket 102 is removed in the expanded or partially expanded configuration. In such embodiments, the expandable basket 102 may be removed or drawn through a catheter with portions of the obstruction 242 positioned or remaining therein. In some embodiments, the intravascular device 100 does not include tethers or other retrieval mechanisms other than a catheter or sheath (e.g., catheter 244 or 240) the expandable basket 102 may be drawn proximally into or through (e.g., directly) for removal in the collapsed configuration. In other embodiments, the intravascular device 100 does not include tethers or other retrieval mechanisms other than a catheter or sheath (e.g., catheter 244) the expandable basket 102 may be drawn proximally into or through (e.g., directly) for removal in the expanded or partially expanded configuration. The expandable basket 102 may be withdrawn from the patient through the catheter or sheath (e.g., the catheter 244 or 240) or simultaneously with the catheter or sheath (e.g., catheter 244 or 240) after it is positioned therein.

Referring to FIG. 3A-FIG. 3B, the intravascular device 100 may also be anchored distal of an obstruction 342 to filter or capture released particulates during another intravascular procedure (e.g., aspiration, mechanical thrombectomy, or breaking up or dissolving an obstruction). For example, during or prior to an aspiration procedure, the intravascular device 100 may be positioned or anchored distal of the obstruction 342 (e.g., thrombus). As described above, the intravascular device 100 may be deployed from the collapsed configuration to the expanded configuration and maintained in substantial opposition with walls of the vessel 346 or vascular (e.g., anchored in position by securing relative axial positions of the inner wire and delivery shaft). During aspiration via an aspiration catheter 344 or other intravascular procedure, released particulates 343 (e.g., fragments that break off or that are not aspirated) of the obstruction 342 may be captured by or within the cavity 112 of the expandable basket 102 of the intravascular device 100 such that distal migration of these released particulates is prevented. As described above, the intravascular device 100 may then be removed or withdrawn in the collapsed or expanded configuration (e.g., using the aspiration catheter 344 or other catheter). The aspiration catheter 344 may be positioned proximal of the proximally oriented cavity 112 or obstruction 342 during aspiration as illustrated in FIG. 3A. In other embodiments, the aspiration catheter 344 may be positioned at least partially within the proximally oriented cavity 112 during aspiration as illustrated in FIG. 3B.

Anchoring the expandable basket 102 within a vessel may be further advantageous in that it may facilitate navigation of a catheter (e.g., a delivery catheter and/or an aspiration catheter) through narrow and/or tortuous pathways, which may be commonly encountered, for example, in the neurovasculature. For example, the relatively small distal end 106 of the expandable basket 102 may be navigated around narrow, tortuous pathways of the neurovasculature in ways that may not be feasible for the larger profile of catheters or sheaths. In this example, the expandable basket 102 may be expanded and inverted once it reaches a target location, at which point it may serve as an anchor point which may be used by an operator to navigate a catheter or sheath (e.g., an aspiration catheter 244) proximal to the target location. For example, once the expandable basket 102 is anchored in this manner, an operator may remove the delivery catheter 240 that introduced the expandable basket 102, but may leave behind the intravascular device 100 e. The operator may then navigate an aspiration catheter 244 over the outer delivery shaft 108 (e.g., coaxially) proximal to the target location. In this example, the expandable basket 102 may exert sufficient outward radial force on the vessel wall in its inverted conformation to allow the operator to advance the aspiration catheter (or any other suitable catheter or sheath) distally with respect to the outer delivery shaft 108 while keeping the expandable basket 102 at or near the target location. In some embodiments, the operator may leave the delivery catheter 240 and may simply introduce the aspiration catheter 244 over the delivery catheter 240. In these embodiments, the aspiration catheter 244 may have a larger diameter than the delivery catheter 240. The efficacy of procedures such as thrombectomy is time dependent, and patient outcomes are directly correlated with reduced recanalization from time of onset. One disadvantage of existing procedures is that they are time- and skill-intensive when it comes to navigating to the site of the lesion. Moreover, vessels of the vasculature—and particularly those of the neurovasculature—are delicate, and can be prone to perforation. The path that the catheter needs to navigate to reach the treatment site follows a long and tortuous route. Additionally, increased time and potential complications may be increased in the event that an aspiration catheter is clogged or needs to be removed and cleaned. The advantage of the anchoring functionality of the intravascular device, when used, is evident when compared to devices that are not so anchored—in such devices, when the aspiration catheter is removed out of the access port, the operator would lose access to the lesion and would need to re-navigate a guidewire to the lesion site, adding time and potential complication to the procedure. The anchoring functionality described here may provide for a fixed, anchored intravascular device 100 that may not require any re-navigation once the expandable basket 102 is anchored. To aid with stability of the anchoring, the intravascular device may also have an extender wire (as described elsewhere herein) to extend the wire enough to allow the operator to hold onto the proximal end of the wire without movement at the distal end to perform an exchange maneuver for removing the delivery catheter. Providing an anchored system as described herein is likely to decrease procedural time and potentially improve outcomes.

Referring to FIG. 4A-FIG. 4B, the intravascular device 100 may also include an integrated aspiration feature. For example, the outer delivery shaft 108 may include one or more apertures or holes 447 positioned on or extending through outer wall or circumference of shaft 108 via which particulates (e.g., captured, filtered, or released) may be aspirated. The one or more holes 447 allow aspiration without a separate or additional aspiration catheter. For example, the outer delivery shaft 108 may be coupled to an aspiration source. As such, in this example, a clinician may not need to position or retrieve an additional aspiration catheter, thus minimizing or reducing steps. As a result, such a device may also be positionable in more narrow or smaller spaces for aspiration relative to devices that require a larger, separate aspiration catheter.

Figure 5:
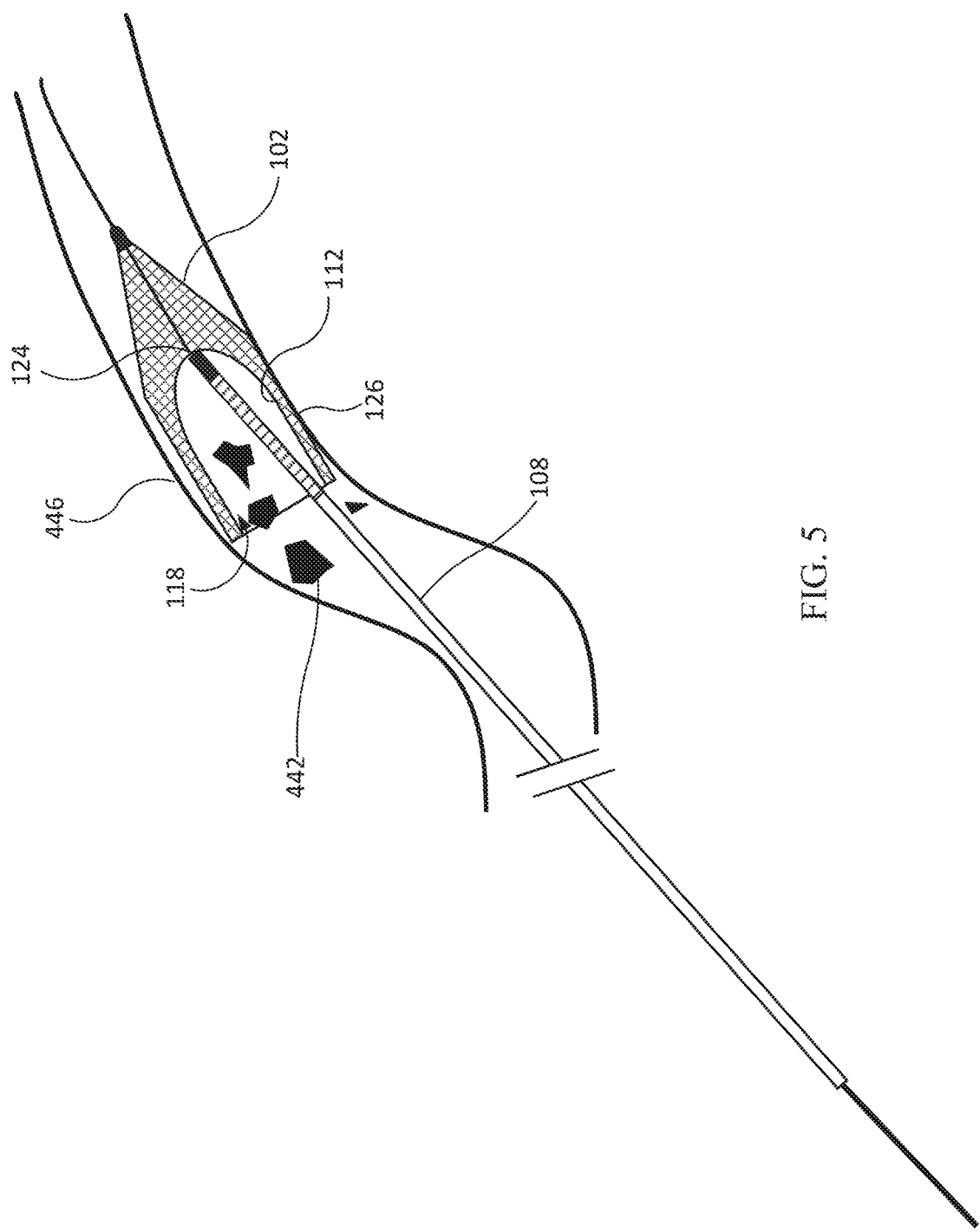
FIG. 5 is an illustration of the intravascular device of FIG. 1A-FIG. 1B within a tortuous vessel in accordance with other aspects of the invention.

Referring to FIG. 5, a lumen or vessel 446 of a patient may be substantially tortuous (e.g., particularly in the neurovasculature). As described herein, the proximally oriented cavity 112 may have a parabolic-shaped cavity 118 formed by the inverted proximal portion 114 within the distal portion 116 of the expandable basket 102. A vertex or apex 124 of the cavity 118 may be pivotally and centrally coupled to the outer delivery shaft 108 (e.g., at a pivot point). This allows the expandable basket 102 to pivot during retrieval of an obstruction 442 with the expandable basket 102 through the lumen 446. As such, the peripheral edge or lip 126 of the basket is maintained in intimate or substantially intimate contact or opposition with a wall of the vessel 346 even within a tortuous segment. Further, the expandable basket remains substantially centered in the vasculature. The obstruction 442 is completely or substantially entirely encapsulated within the proximally oriented cavity 112. This prevents or reduces a likelihood of the obstruction 442 or fragments of the obstruction from escaping between a gap between the basket 102 and the vessel wall that may form a distal embolization.

Figure 6A:
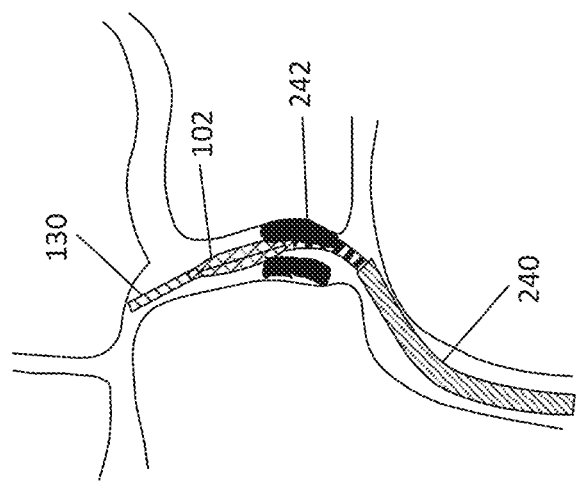
Figure 6B:
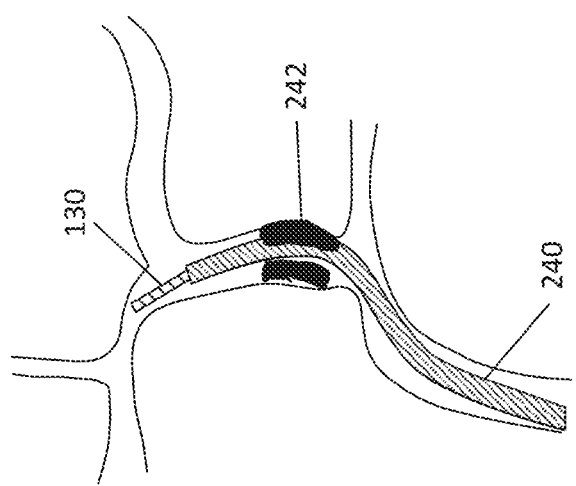
Figure 6C:
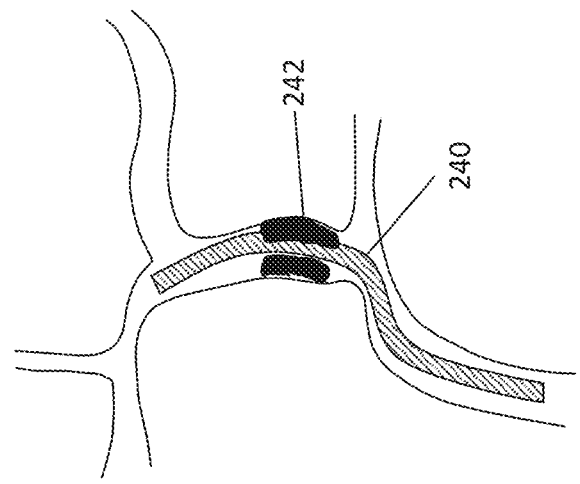
Figure 6F:
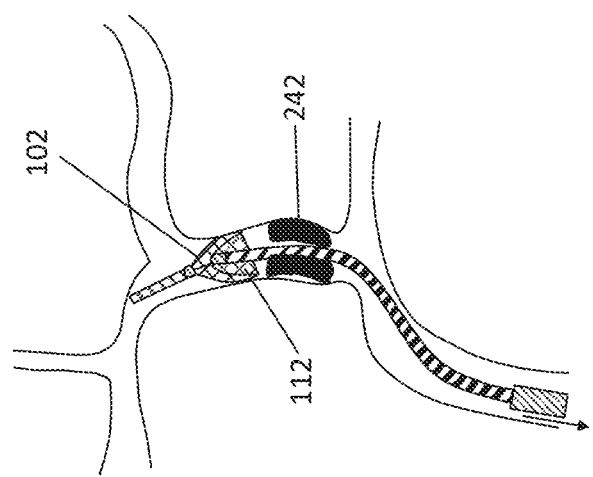
Figure 6E:
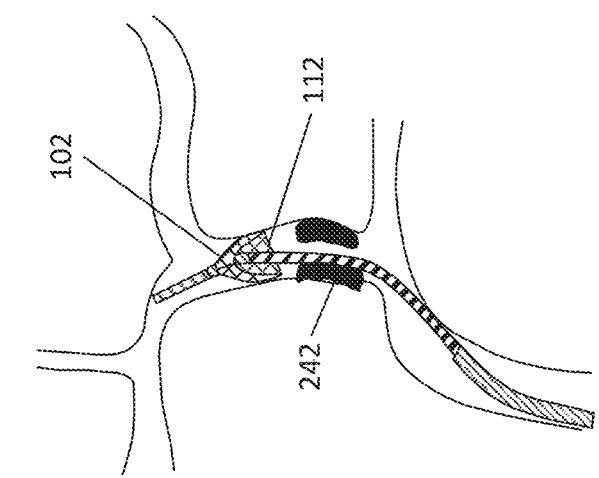
Figure 6D:
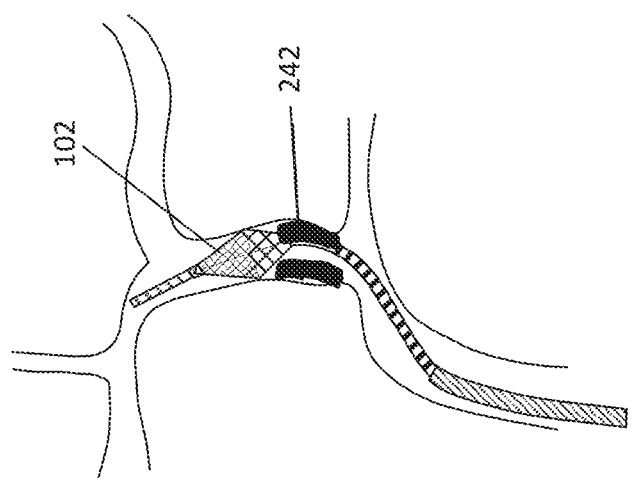

FIG. 6A-FIG. 6J illustrate an example embodiment where the expandable basket 102 of the intravascular device 100 is used as a filter to aid the aspiration of an obstruction 242. As shown in FIG. 6A, a delivery catheter 240 may be navigated past an obstruction 242 (for example, a thrombus). As shown in FIG. 6B and FIG. 6C, the expandable basket 102 may be fully extended out of the delivery catheter 240, with the entirety of the expandable basket 102 being positioned distal to the destruction 242. The expandable basket 102 may be substantially in its delivery configuration. As shown in FIG. 6D, the expandable basket 102 may be transitioned from its delivery configuration to a partially expanded configuration. As shown in FIG. 6E, the expandable basket 102 may be inverted into its expanded configuration, creating the proximally oriented cavity 112. The expandable basket 102 may be anchored within the vessel at this location. As shown in FIG. 6F, the delivery catheter 240 may be retracted (e.g., using an extender wire, as described further herein, for example, with respect to FIG. 8A-FIG. 8C), leaving behind the intravascular device including the inverted expandable basket 102. As shown in FIG. 6G and FIG. 6H, an aspiration catheter may be advanced distally over the outer delivery shaft 108 of the intravascular device to approach the obstruction 242 (e.g., making use of an extender wire). As shown in FIG. 6I, the aspiration catheter 244 may create suction the last to aspirate the obstruction 242. In some embodiments, the suction may cause the obstruction 242 to fragment, and the aspiration catheter 244 may aspirate the fragments 243, as shown in FIG. 6I. As shown in FIG. 6J the aspiration catheter 244 may be advanced into the proximally oriented cavity 112, and may be navigated all the way to the dome formed by the expandable basket 102. In some embodiments, at least a portion of the expandable basket 102 may "cup" (e.g., substantially circumscribe or surround) a distal portion of the aspiration catheter 244 when the aspiration catheter 244 is advanced into proximally oriented cavity 112 up to the distal end of the proximally oriented cavity 112 (e.g., which may be in the shape of a dome or funnel). This cupping of the distal portion of the aspiration catheter 244 may be advantageous in that it may allow the aspiration catheter 244 to aspirate the entire obstruction 242 without leaving room for the release of fragments or particulates distally (e.g., around the expandable basket 102). The ability to cup the distal portion of the aspiration catheter 244 may allow for enhanced constraint of the obstruction 242 during the entire aspiration process, and therefore may provide additional security in retrieval of the obstruction 242 without the release of fragments or particulates distally. In its expanded configuration, the expandable basket 102 may extend radially outward to contact a vessel wall distal to the thrombus (or other obstruction) being retrieved, and may effectively create a seal against the vessel wall to prevent emboli from being released distally. This seal may be maintained while the aspiration catheter is advanced all the way up to the dome of the proximally oriented cavity 112, such that all of the thrombus may be aspirated while preventing emboli from being released distally. The basket shape of the device is particularly advantageous when compared to other devices that do not have such a shape (e.g., relatively flat formations, stent formations), because it enhances the ability of the device to capture an obstruction 242 or any distal fragments that may be released from such obstruction 242 during a procedure. Embodiments of the intravascular device 100 where the expandable basket 102 is centrally coupled to the outer delivery shaft 108 may be particularly suited to allow for the navigation of the aspiration catheter 244 up to the dome formed by the expandable basket 102 and for the cupping of the aspiration catheter 244 by the expandable basket 102. These embodiments allow for the aspiration catheter 244 to advance unencumbered toward the expandable basket 102, unlike other devices that may employ, for example, tethers or other features that may branch radially outward from a delivery shaft of the device (because such features would be deflected and may consequently, for example, deflect or close the expandable basket 102).

Although FIG. 6G-FIG. 6J illustrate an example embodiment where the aspiration catheter 244 is advanced distally toward the proximally oriented cavity 112 of the expandable basket 102 while the expandable basket 102 is maintained in a fixed position, this disclosure also contemplates withdrawing the expandable basket 102 proximally toward the aspiration catheter 244 while the aspiration catheter 244 is maintained in a fixed position. For example, the expandable basket 102 may be withdrawn proximally toward the aspiration catheter 244 until at least a portion of the expandable basket 102 may "cup" or surround a distal portion of the aspiration catheter 244. This disclosure also contemplates performing both types of movements, for example, alternating between retracting the expandable basket 102 and advancing the aspiration catheter 244.

Figure 6M:
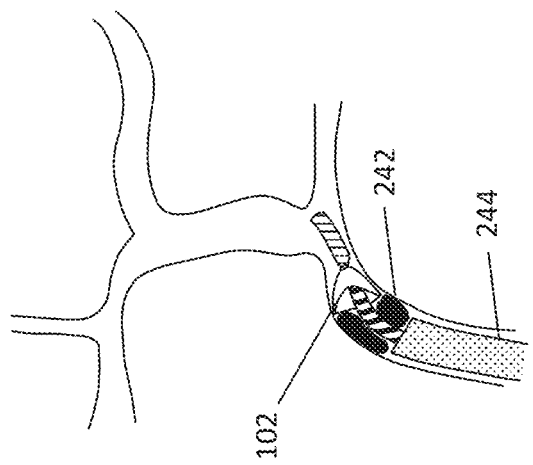
FIG. 6K-FIG. 6M illustrate example embodiments where the inverted expandable basket may serve to cap at least a distal portion of an obstruction and retrieve the obstruction as a whole.
Figure 6L:
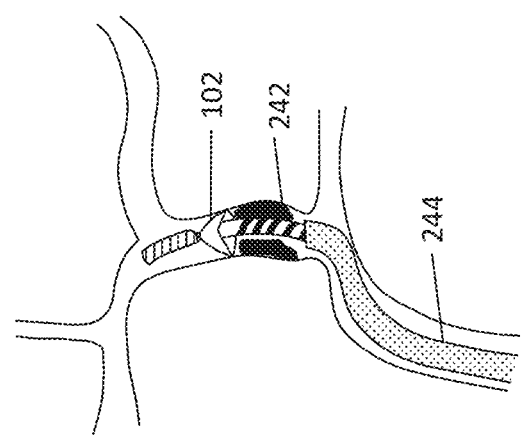
Figure 6K:
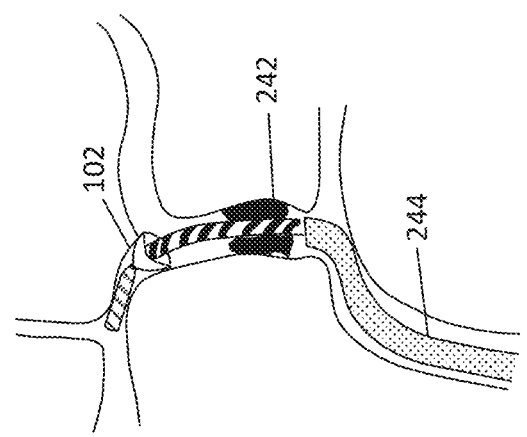

The example embodiment discussed above with respect to FIG. 6G-FIG. 6J illustrate an example where the obstruction 242 is fragmented, with the resulting fragments being aspirated. In other embodiments, the obstruction 242 may be removed without fragmenting the obstruction. In these embodiments, the suction strength may be adjusted (for example, it may be decreased to a predetermined value) to prevent the obstruction 242 from fragmenting, and the obstruction 242 may be extracted as a whole. FIG. 6K-FIG. 6M illustrates such embodiments, where the inverted expandable basket 102 may serve to "cap" (e.g., constrain or envelop) at least a distal portion of the obstruction 242 at the distal end and retrieve the obstruction 242 as a whole. For example, as shown in FIG. 6L, the expandable basket 102 may be moved proximally toward the aspiration catheter 244 to "cap" the obstruction 242 by constraining a distal portion of the obstruction 242. The expandable basket 102 may be made to encapsulate at least a portion of the obstruction 242 within the proximally oriented cavity 112. In this example, as shown in FIG. 6M, the aspiration catheter 244 and the expandable basket 102 may then be retrieved proximally together as a system while maintaining the integrity of the obstruction 242. Removing the obstruction 242 without fragmenting the obstruction 242 may be advantageous in that, for example, it may reduce the likelihood of the formation of particulates which are more likely to escape beyond the expandable basket 102 than a non-fragmented single/whole obstruction that is removed substantially intact.

Figure 7A:
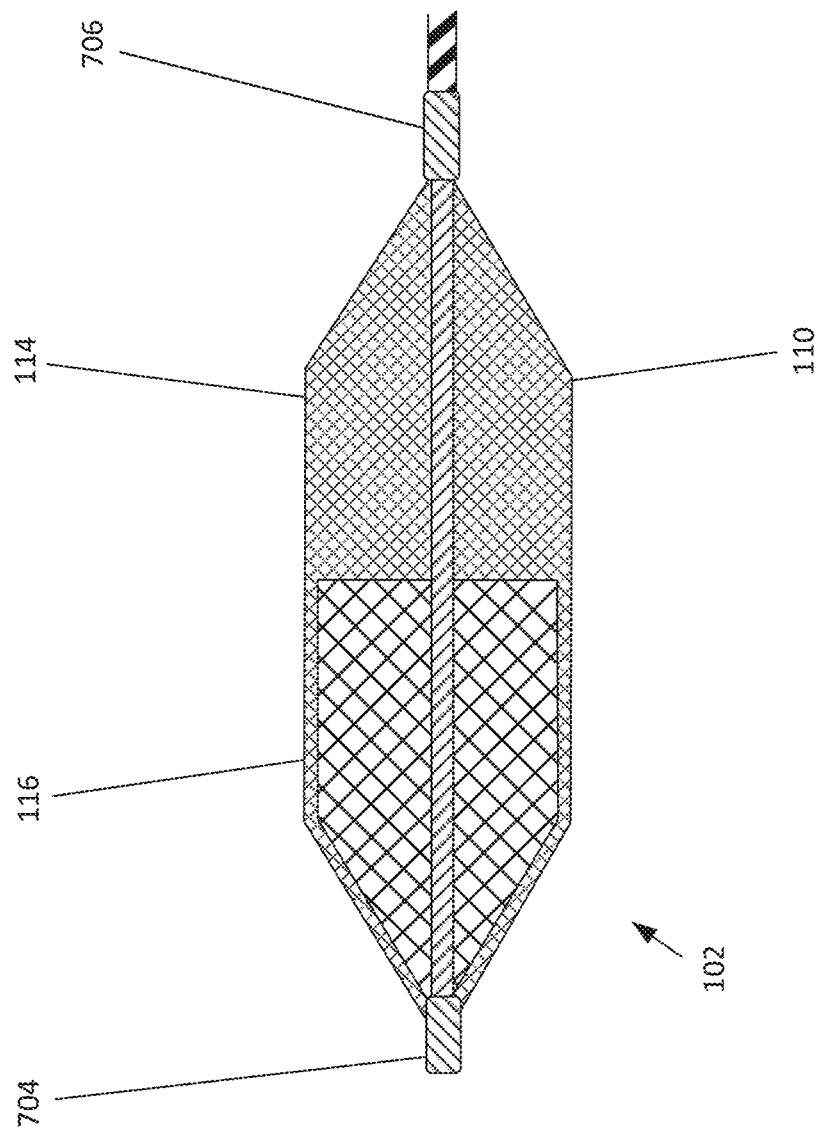
FIG. 7A illustrates a close-up image of the expandable basket in its partially expanded configuration.

FIG. 7A illustrates a close-up image of an example expandable basket 102 in its partially expanded configuration. The distal portion 116 may include a first number of layers and the proximal portion 114 may include a second number of layers. In some embodiments, the first number of layers is greater than second number of layers. For example, the distal portion 116 may include two layers, while the proximal portion 114 may include only a single layer. In some embodiments, the difference in layers may be due to one or more extra layers being present in a portion of the expandable basket 102. For example, the expandable basket 102 may include an outer layer that extends throughout the expandable basket 102, and an inner layer that is present only in the distal portion 116. Any suitable materials may be used for makeup the different layers. For example, a first layer (for example, the outer layer) may be made of 75% cobalt-chromium or 35N LT alloy and 25% platinum-tungsten, and a second layer (for example, the inner layer) may be made of 100% drawn filled tubing (DFT). As illustrated in FIG. 7A, the layers may be made up of a number of strands or braids. The number of strands may vary, for example, based on a size of the expandable basket 102. For example in expandable basket 102 of a relatively large diameter may be made up of a larger number of strands than in expandable basket 102 of a relatively small diameter. As illustrated in FIG. 7A, the inner wire 110 may extend through the expandable basket 102. The portion of the inner wire 110 that extends distally from the expandable basket 102 may be surrounded by a coil 132. For marking purposes, there may be a distal marker band 704 at or near the distal end of the expandable basket 102 and a proximal marker band 706 at the proximal end of the expandable basket 102.

Figure 7B:
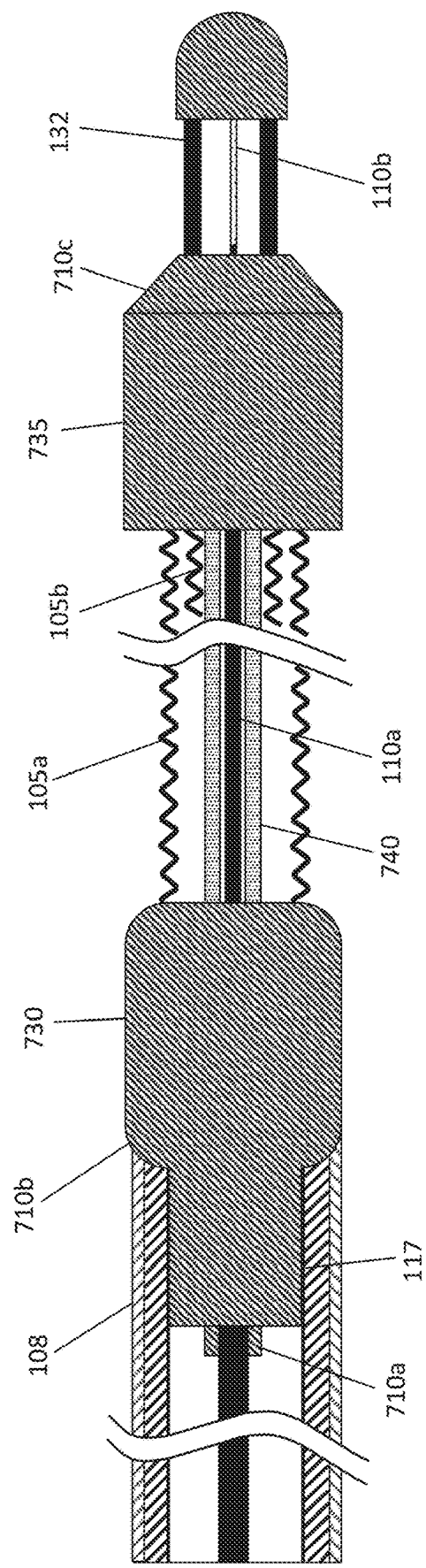
FIG. 7B illustrates an example embodiment of an intravascular device with various components, some of which are radiopaque.

FIG. 7B illustrates an example embodiment of an intravascular device with various components, some of which are radiopaque. Many existing intravascular devices do not provide an adequate level of radiopacity at a distal portion, making it difficult for an operator to visualize and manipulate the devices. This is especially an issue when operating in narrow and tortuous pathways, such as those of the neurovascular. To address this problem, some embodiments of the present invention may include an intravascular device 100 having several radiopaque components in several areas at a distal portion of the intravascular device 100. These radiopaque components may be useful in allowing for visualization of the distal mechanism prior to and/or during use as a filter, anchor, and/or obstruction-retrieving device. In some embodiments, referencing FIG. 7B, the intravascular device 100 may include a marker band 117 that is connected to a portion of the inner wire 110a by a solder joint 710a. The marker band 117 may be coupled to an inner perimeter of the outer delivery shaft 108. The marker band 117 may also be coupled to a proximal anchoring element 730, which may itself be coupled to the outer delivery shaft 108 by a solder joint 710b. The proximal anchoring element 730 may further be coupled to the proximal portion of the expandable basket (portions of an inner layer 105a and an outer layer 105b of the expandable basket are illustrated in FIG. 7B). In these embodiments, as illustrated in FIG. 7B, the marker band 117 may be used as part of a connection mechanism for connecting the expandable basket to the outer delivery shaft 108. In some embodiments, the proximal anchoring element 730 may be coupled to a proximal portion of the expandable basket by any suitable means. For example, the proximal anchoring element 730 may circumscribe the proximal portion of the expandable basket and thereby be affixed to the proximal portion of the expandable basket. In some embodiments, the distal portion of the expandable basket may be coupled to a distal anchoring element 735 (for example, in a similar manner to the proximal anchoring element 730). In some embodiments, a supporting coil 740 may extend between the proximal anchoring element 730 and the distal anchoring element 735. In some embodiments, the distal anchoring element 735 may itself be coupled via a solder joint 710c to the coil 132, which may extend to the distal tip of the intravascular device 100. The coil 132 may be used, for example, to surround and protect the distal portion of the inner wire 110b (which may be a flattened portion as explained elsewhere herein). In some embodiments, the proximal anchoring coil 730 and/or the distal anchoring coil 735 may be coils. In some embodiments, the marker band 117, the proximal anchoring element 730, the distal anchoring element 735, the inner layer 105a, the outer layer 105b, the supporting coil 740, and the coil 132 may all be radiopaque. Such embodiments may be particularly advantageous in that the radiopaque components may provide total or near-total visualization of important junctures of the entire distal mechanism prior to and/or during use as a filter, anchor, and/or obstruction-retrieving device. In other embodiments, any suitable combination of the marker band 117, the proximal anchoring element 730, the distal anchoring element 735, the inner layer 105a, the outer layer 105b, the supporting coil 740, and the coil 132 may be made radiopaque as necessary.

FIG. 8A-FIG. 8C illustrate an example embodiment of an extender wire 810 that is configured to releasably couple to the intravascular device (e.g., to the inner wire 110 of the intravascular device). The extender wire 810 may be useful for the process of removing catheter or exchanging a catheter quickly and efficiently. For example, the extender wire 810 may be used when the delivery catheter 240 is exchanged for the aspiration catheter 244. In some embodiments, the extender wire 810 may be coupled to the inner wire 110 via extender hypotubes 820, as illustrated in FIG. 8. This coupling of the extender wire 810 to the inner wire 110 is illustrated in FIG. 8B-FIG. 8C, which show a close-up view of the extender hypotubes 820, the extender wire 810, and the inner wire 110. In these embodiments, following the coupling of the extender wire to the extender hypotubes 820, the delivery catheter 240 may be removed by retrieving it proximally over the extender hypotubes 820. An operator may be able to hold onto the extender wire 810, thereby maintaining the position of the inner wire 110 (and the expandable basket 102 at the distal end) as the delivery catheter 240 is removed completely. The aspiration catheter 244 may then be advanced over the extender wire 810, over the extender hypotubes 820, and finally over the intravascular device 100, all without significantly affecting the position of the expandable basket 102. The aspiration catheter 244 may then be quickly navigated to the location of the expandable basket 102, using the expandable basket 102 as an anchor point for advancing the aspiration catheter 244.

Figure 9F:
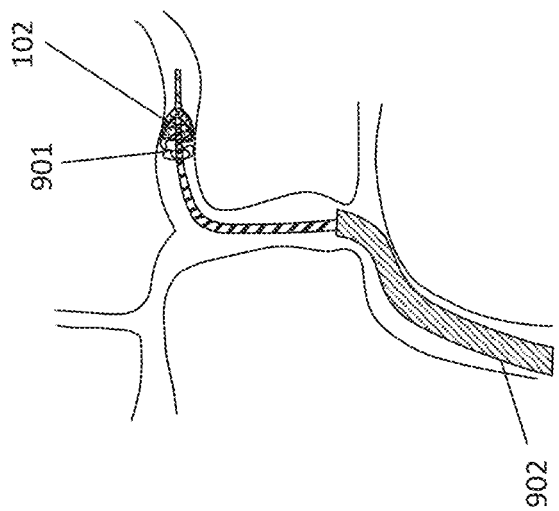
Figure 9E:
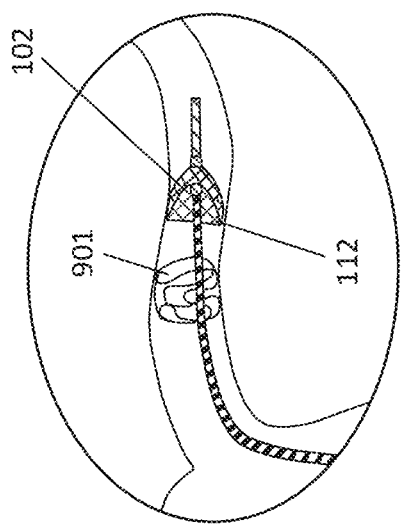
Figure 9D:
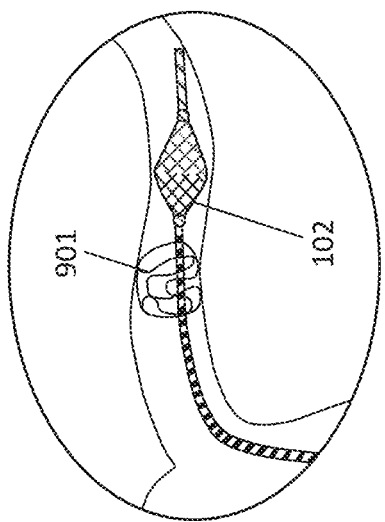

FIG. 9A-FIG. 9F illustrate an example embodiment where the expandable basket 102 is used to retrieve a foreign object other than a thrombus or some other naturally occurring obstruction. FIG. 9A-FIG. 9F illustrate the retrieving of a coil mass 901 that may have been part of a treatment for an aneurysm. In this example, the coil mass 901 may have become dislodged from an aneurysm, and may be obstructing a vessel, as illustrated in FIG. 9A. As shown in FIG. 9B the delivery catheter 240 may be navigated distally past the coil mass 901. The expandable basket 102 may then be caused to exit the delivery catheter 240. As shown in FIG. 9C, the expandable basket 102 may be fully extended out of the delivery catheter 240, with the entirety of the expandable basket 102 being positioned distal to the coil mass 901. As shown in FIG. 9D, the expandable basket 102 may be transitioned from its delivery configuration to a partially expanded configuration. As shown in FIG. 9E, the expandable basket 102 may be inverted into its expanded configuration, creating the proximally oriented cavity 112. As shown in FIG. 9F, the coil mass 901 may then be captured within the proximally oriented cavity 112, and may then be retrieved by, for example, the catheter 902. The catheter 902 be any suitable catheter of sufficient size to receive the coil mass 901. In some embodiments, the catheter 902 may be an aspiration catheter 244.

Figure 10:
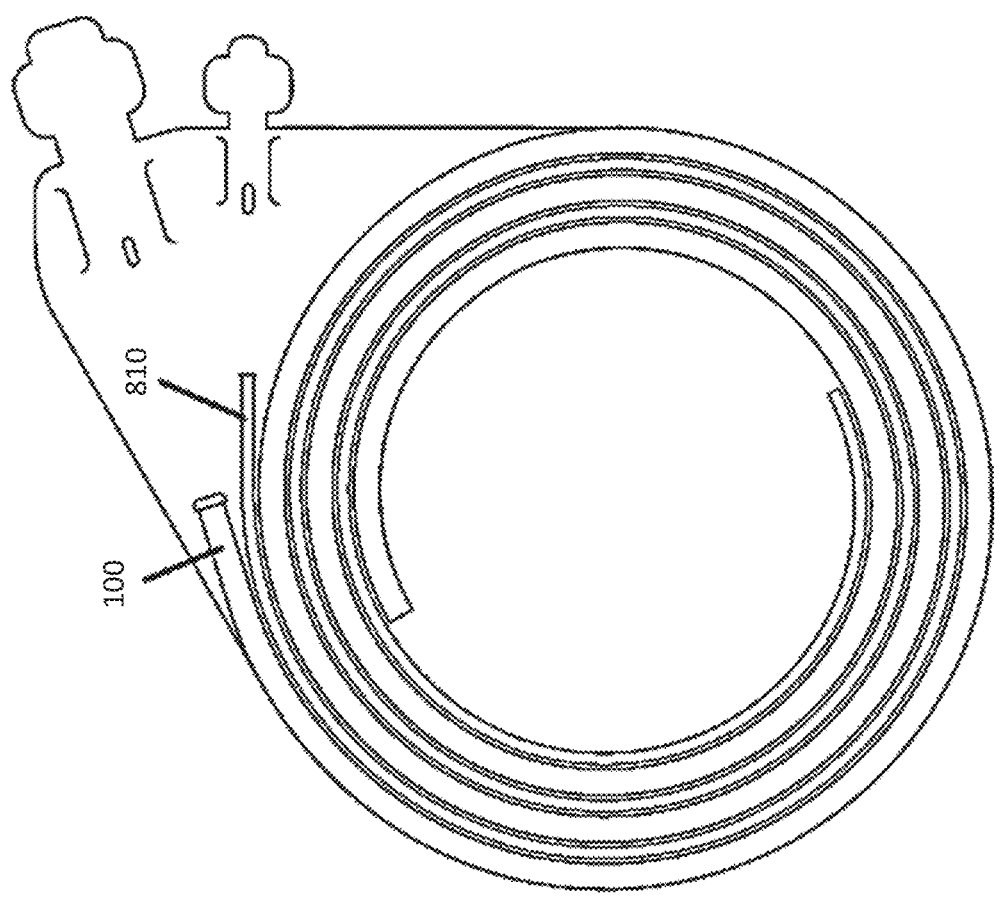
FIG. 10 illustrates a kit that includes the intravascular device and the extender wire.

FIG. 10 illustrates a kit that includes the intravascular device 100 and the extender wire 810. As illustrated in FIG. 10, the intravascular device 100 and the extender wire 810 may be coiled so as to form in interleaved spiral within a single package. As illustrated, both the intravascular device 100 and the extender wire 810 may be coiled around a single axis. This manner of packaging may be advantageous in that it may save space and in that it packages necessary components together and easily within reach. Although FIG. 10 illustrates only the inclusion of the intravascular device 100 the extender wire 810, any other suitable catheter or sheathe may be included within the packaging, for example as part of the interleaved spiral. Likewise, although FIG. 10 illustrates only the inclusion of two elements in the interleaved spiral (for example, the intravascular device 100 and the extender wire 810), this disclosure contemplates the inclusion of more than two elements (for example, the intravascular device 100, the extender wire 810, and the aspiration catheter 244).

Figure 11:
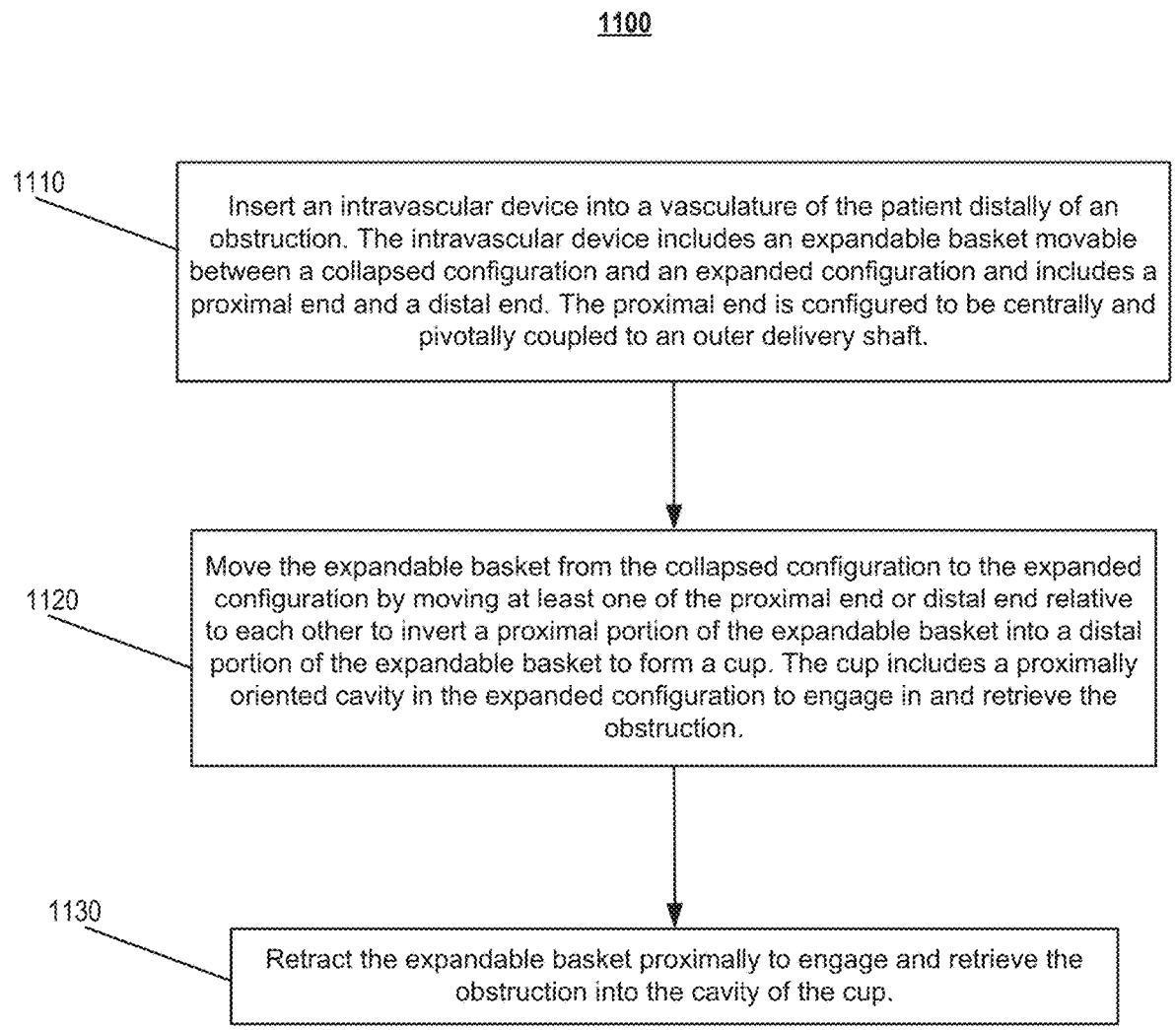
FIG. 11 is a flowchart illustrating an exemplary method of retrieving an obstruction with an embodiment of the intravascular device described herein.

FIG. 11 is a flowchart illustrating an example method 1100 for engaging and retrieving an obstruction from a patient's vasculature with the intravascular device 100 as described herein (e.g., retrieving a thrombus from a patient's neurovasculature). One or more of any steps of method 1100 may be removed, re-ordered, substituted, added, or modified. The method 1100 for retrieving an obstruction from a vasculature (e.g., a neurovascular chair) of a patient is provided that includes step 1110, which includes advancing an intravascular device (e.g., a neurovascular device) into a vasculature of the patient distally of an obstruction. The intravascular device may include an expandable basket movable between a collapsed configuration and an expanded configuration and having a proximal end and a distal end. The proximal end may be configured to be centrally and pivotally coupled to an outer delivery shaft. The method may include, at step 1120, deploying the expandable basket from the collapsed configuration to the expanded configuration by moving at least one of the proximal end or distal end relative to each other to invert a proximal portion of the expandable basket towards a distal portion of the expandable basket to form a proximally oriented cavity. The proximally oriented cavity may include a proximally oriented cavity in the expanded configuration to engage and retrieve the obstruction. At step 1130, the method includes retracting the expandable basket proximally to engage and retrieve the obstruction into the cavity of the proximally oriented cavity. The method may further include the steps of aspirating or otherwise removing or retrieving the obstruction from the proximally oriented cavity. In some embodiments, the method includes withdrawing or removing the intravascular device 100 (e.g., the basket 102) from the patient. This may include moving the expandable basket 102 to the collapsed configuration from the expanded configuration and withdrawing the expandable basket 102 proximally through a catheter (e.g., aspiration catheter, delivery catheter, or other suitable catheters).

FIG. 12 is a flowchart illustrating an example method 1200 for filtering at least one particulate in a vasculature of a patient, where the particulate may be released during a procedure performed upon a patient. The filtering may be done to prevent migration of the at least one released particulate. At step 1210, an intravascular device may be advanced into a vasculature of the patient. The intravascular device may include an expandable basket movable between a collapsed configuration and an expanded configuration and having a proximal end and a distal end. The proximal end is configured to be centrally and pivotally coupled to an outer delivery shaft. At step 1220, the expandable basket may be deployed from the collapsed configuration to the expanded configuration by moving at least one of the proximal end or distal end relative to each other to invert a proximal portion of the expandable basket toward a distal portion of the expandable basket to form a proximally oriented cavity in the expanded configuration. At step 1230, the intravascular device may optionally be anchored within the vasculature at a location distal of an obstruction (e.g., a thrombus). This anchoring may be carried out, for example, by an outward radial force of the expandable basket against the neurovasculature resulting from the expandable basket being in the expanded configuration. At step 1240, the at least one released particulate may be captured within the proximally oriented cavity of the expandable basket. While referring in particular to engaging, retrieving, filtering, anchoring, or capturing obstructions or particulates within the neurovasculature (e.g., lumen or vessel within head, neck, or brain) of the patient, the present invention is not limited to any specific context. For example, such devices and methods disclosed herein may be used in the coronary or pulmonary vasculature (e.g., to retrieve a pulmonary embolism), the peripheral vasculature (e.g., to retrieve a deep vein thrombus), or in the context of other procedures (e.g., vasospasm, carotid stenting, angioplasty, temporary vessel occlusion, aneurysm bridging, aortic/mitral valve repair or implantation, interventional cardiology procedures). For example, the intravascular device may be used as a filtering device (e.g., instead of or in addition to as a mechanical thrombectomy device) to protect a patient from distal emboli during the thrombectomy procedure or removal of the obstruction, aspiration, or other procedures (e.g., cardiac procedures such as valve replacement, breaking up or dissolution of a thrombus or other obstruction). The intravascular device may be used as a flow diverter or vascular plug in other embodiments (e.g., with pores of the mesh or braid sized accordingly to allow or prevent blood flow therethrough).

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The term "or" in reference to a list of two or more items, covers all of the following interpretations of the word: any of the items in the list, all of the items in the list, and any combination of items in the list. The terms "comprising," "having," "including," and "containing" are to be construed as open-ended terms (i.e., meaning "including, but not limited to,") unless otherwise noted. The terms "connected" or "attached" are to be construed as partly or wholly contained within, coupled to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. All references, including publications, patent applications, and patents, cited herein are hereby incorporated by reference to the same extent as if each reference were individually and specifically indicated to be incorporated by reference and were set forth in its entirety herein.

What is claimed is:

1. A method for filtering particulates released during a neurovascular procedure performed upon a patient to prevent distal migration of the released particulates, the method comprising:
    advancing a neurovascular device into a neurovasculature of the patient, the neurovascular device comprising an expandable basket movable between a collapsed configuration and an expanded configuration and having a proximal end and a distal end, the proximal end configured to be centrally and pivotally coupled to an outer delivery shaft,
    wherein the expandable basket comprises an inner layer and an outer layer, wherein the inner layer is configured to expand to a larger diameter relative to the outer layer when the expandable basket is moved to a partially expanded configuration between the collapsed configuration and expanded configuration;
    deploying the expandable basket from the collapsed configuration to the expanded configuration by moving at least one of the proximal end or distal end relative to each other to invert a proximal portion of the expandable basket towards a distal portion of the expandable basket to form a proximally oriented cavity in the expanded configuration;
    anchoring the neurovascular device distal of a thrombus; and
    capturing the released particulates of the thrombus within the proximally oriented cavity of the expandable basket.

2. The method of claim 1, wherein anchoring the neurovascular device is carried out by an outward radial force of the expandable basket against the neurovasculature when the expandable basket is in the expanded configuration.

3. The method of claim 2, wherein an outside perimeter of the expandable basket intimately contacts a wall of the neurovasculature to maintain vessel opposition and fixation of the expandable basket.

4. The method of claim 2, further comprising repositioning or adjusting an anchor position of the neurovascular device distal of the thrombus.

5. The method of claim 2, wherein anchoring the neurovascular device is carried out without blocking blood flow within the neurovasculature.

6. The method of claim 2, further comprising withdrawing a delivery catheter through which the neurovascular device was advanced and navigating an aspiration catheter toward the anchored expandable basket, wherein the anchored expandable basket provides a substantially fixed pre-positioned guide to the thrombus.

7. The method of claim 2, further comprising tracking an aspiration catheter over the outer delivery shaft of the neurovascular device.

8. The method of claim 7, further comprising aspirating the thrombus while distally advancing the aspiration catheter toward the expandable basket.

9. The method of claim 8, wherein capturing comprises filtering the released particulates of the thrombus within the proximally oriented cavity during the aspirating.

10. The method of claim 9, further comprising advancing the aspiration catheter distally toward the expandable basket such that at least a portion of the expandable basket cups a distal portion of the aspiration catheter while the expandable basket is anchored.

11. The method of claim 9, wherein the distal portion of the aspiration catheter comes in contact with the proximally oriented cavity of the expandable basket in the expanded configuration.

12. The method of claim 1, wherein the proximal end of the expandable basket is pivotally coupled to the outer delivery shaft at a distal portion of the outer delivery shaft.

13. The method of claim 1, wherein the neurovascular device comprises an inner core wire extending coaxially through the outer delivery shaft, a distal portion of the inner core wire coupled to the distal end of the expandable basket.

14. The method of claim 13, further comprising locking a position of the outer delivery shaft relative to a position of the inner core wire after the proximally oriented cavity is formed to maintain the expandable basket in the expanded configuration.

15. The method of claim 13, further comprising releasably coupling an extender wire to the inner core wire.

16. The method of claim 15, wherein the extender wire is releasably coupled to the inner core wire via one or more extender hypotubes.

17. The method of claim 15, further comprising exchanging a delivery catheter for an aspiration catheter over the extender wire.

18. The method of claim 1, wherein deploying the expandable basket from the collapsed configuration to the expanded configuration comprises moving the proximal end of the expandable basket axially towards the distal end of the expandable basket to invert the proximal portion of the expandable basket towards the distal portion of the expandable basket to form the proximally oriented cavity.

19. The method of claim 1, wherein deploying the expandable basket from the collapsed configuration to the expanded configuration comprises moving the distal end of the expandable basket axially towards the proximal end of the expandable basket to invert the proximal portion of the expandable basket towards the distal portion of the expandable basket to form the proximally oriented cavity.

20. The method of claim 1, wherein deploying the expandable basket from the collapsed configuration to the expanded configuration comprises moving the expandable basket to a partially expanded configuration between the collapsed configuration and the expanded configuration prior to moving at least one of the proximal end or distal end relative to each other, wherein the expandable basket is not constrained by a delivery catheter or sheath extending around at least a portion of the expandable basket.

21. The method of claim 1, wherein the expandable basket comprises support ribs.

22. The method of claim 1, wherein a distal portion of the expandable basket comprises a pre-set conical configuration.

23. The method of claim 1, wherein the expandable basket is constructed from a radiopaque material.

24. The method of claim 1, wherein advancing the neurovascular device comprises positioning the expandable basket distal to the thrombus in the collapsed configuration.

25. The method of claim 24, further comprising:
    aspirating or removing the thrombus, wherein capturing comprises filtering into the proximally oriented cavity particulates released during aspiration or removal of the thrombus to prevent distal migration of particulates of the thrombus.

26. The method of claim 24, further comprising moving the expandable basket to the collapsed configuration from the expanded configuration for withdrawal from the patient after removal of at least a portion of the thrombus.

27. The method of claim 26, further comprising withdrawing the expandable basket in the collapsed configuration from the patient.

\* \* \* \* \*